US012782276B2

(12) United States Patent
Fujie et al.

(10) Patent No.: US 12,782,276 B2
(45) Date of Patent: Nov. 3, 2026

(54) OPTICAL SENSOR CHIP, OPTICAL SENSOR SYSTEM, AND MEASUREMENT METHOD

(71) Applicant: Mitsubishi Electric Corporation, Tokyo (JP)

(72) Inventors: Akihiro Fujie, Tokyo (JP); Hiroshi Otsuka, Tokyo (JP); Masayuki Baba, Tokyo (JP); Toshiyuki Ando, Tokyo (JP); Hitomi Ono, Tokyo (JP); Yuta Takemoto, Tokyo (JP)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 50 days.

(21) Appl. No.: 18/802,790

(22) Filed: Aug. 13, 2024

(65) Prior Publication Data

US 2024/0402082 A1 Dec. 5, 2024

Related U.S. Application Data

(63) Continuation of application No. PCT/JP2022/013782, filed on Mar. 24, 2022.

(51) Int. Cl.

*G01N 21/41* (2006.01)
*G01D 5/26* (2006.01)
(Continued)

(52) U.S. Cl.

CPC ............. *G01N 21/41* (2013.01); *G01D 5/268* (2013.01); *G01N 33/246* (2013.01); *G02B 6/29338* (2013.01); *G02F 1/212* (2021.01)

(58) Field of Classification Search

CPC ... G02F 1/212; G02B 6/2935; G02B 6/29338; G01N 33/246; G01N 21/41; G01D 5/268
See application file for complete search history.

(56) References Cited

U.S. PATENT DOCUMENTS 11,105,980 B1 * 8/2021 Hu ...................... H04J 14/0209
2014/0321502 A1 10/2014 Ahmed et al.
(Continued)

FOREIGN PATENT DOCUMENTS

CN 107870400 A * 4/2018 ........... G02B 6/4204
DE 11 2022 006 679 T5 12/2024
(Continued)

OTHER PUBLICATIONS

Kamal Sarabandi, Microstrip Ring Resonator for Soil Moisture Measurements, 1997 (Year: 1997).*
(Continued)

*Primary Examiner* — Maurice C Smith
(74) *Attorney, Agent, or Firm* — Birch, Stewart, Kolasch & Birch, LLP

(57) ABSTRACT

An optical sensor chip includes a spot-size conversion unit to receive a first optical signal from outside, a changer unit to change the first optical signal depending on a state of a specimen, a spot-size conversion unit to output the first optical signal to the outside, a spot-size conversion unit to receive a second optical signal from the outside, a multiplexer unit to multiplex a first optical signal changed by the changer unit depending on the state of the specimen and the second optical signal, and a spot-size conversion unit to output an optical signal multiplexed by the multiplexer unit to the outside.

14 Claims, 18 Drawing Sheets

(51) Int. Cl.

| | |
|---|---|
| ***G01N 33/24*** | (2006.01) |
| ***G02B 6/293*** | (2006.01) |
| ***G02F 1/21*** | (2006.01) |

(56) References Cited

U.S. PATENT DOCUMENTS

| | | | |
|---|---|---|---|
| 2016/0265898 A1 | 9/2016 | Schreuder et al. | |
| 2016/0336718 A1* | 11/2016 | Takabayashi | H01S 5/0078 |
| 2019/0234850 A1 | 8/2019 | Singh et al. | |
| 2020/0386718 A1 | 12/2020 | Singh et al. | |
| 2021/0401291 A1 | 12/2021 | Schriek et al. | |
| 2025/0137992 A1 | 5/2025 | Hayashi et al. | |

FOREIGN PATENT DOCUMENTS

| | | | |
|---|---|---|---|
| JP | 8-219989 A | 8/1996 | |
| JP | 2011-107071 A | 6/2011 | |
| JP | 2022-506275 A | 1/2022 | |
| WO | WO 2015/015149 A1 | 2/2015 | |
| WO | WO 2020/094265 A1 | 5/2020 | |
| WO | WO-2021038407 A1 * | 3/2021 | G01D 5/35364 |

OTHER PUBLICATIONS

German Office Action for German Application No. 11 2022 006 491.9, dated Apr. 15, 2025, with English translation.

International Search Report, issued in PCT/JP2022/013782, PCT/ISA/210, dated May 31, 2022.

Notice of Reasons for Refusal for Japanese Application No. 2022-566312, dated Nov. 29, 2022.

German Office Action for German Application No. 11 2022 006 491.9, dated Apr. 8, 2026, with English translation.

* cited by examiner

OPTICAL SENSOR CHIP, OPTICAL SENSOR SYSTEM, AND MEASUREMENT METHOD

CROSS REFERENCE TO RELATED APPLICATIONS

This application is a Continuation of PCT International Application No. PCT/JP2022/013782, filed on Mar. 24, 2022, all of which is hereby expressly incorporated by reference into the present application.

TECHNICAL FIELD

The present disclosure relates to an optical sensor chip, an optical sensor system, and a measurement method.

BACKGROUND ART

In recent years, the technique of nondestructively measuring the state of a specimen has become widespread. For example, Patent Literature 1 describes a detection device including an optical sensor and an optical switch. In the detection device, a plurality of objects to be measured are connected to the optical switch, and by controlling the optical switch to switch the objects to be measured, the optical sensor measures the objects to be measured.

CITATION LIST

Patent Literatures

Patent Literature 1: WO 2015/015149

SUMMARY OF INVENTION

Technical Problem

In the optical sensor included in the detection device described in Patent Literature 1, in order to measure each of a plurality of objects to be measured, it is necessary to sequentially switch the objects to be measured using the optical switch. For this reason, there is a problem that even if a plurality of the optical sensors described in Patent Literature 1 are used, the state of a plurality of portions of a specimen cannot be collectively measured.

The present disclosure has been made to solve the above problems, and an object thereof is to obtain an optical sensor chip capable of being used to collectively measure the state of a plurality of portions of a specimen.

Solution to Problem

An optical sensor chip according to the present disclosure, capable of taking an arbitral connection form via a connector, includes a first interface to receive a first optical signal from outside via an optical fiber, a changer to change the first optical signal depending on a state of a specimen, a second interface to output the first optical signal to the outside via an optical fiber, a third interface to receive a second optical signal from the outside via an optical fiber, a multiplexer to multiplex a first optical signal changed by the changer depending on the state of the specimen and the second optical signal received by the third interface, and a fourth interface to output an optical signal multiplexed by the multiplexer to the outside via an optical fiber.

Advantageous Effects of Invention

According to the present disclosure, the specimen is disposed in an optical sensor unit in which a plurality of optical sensor chips are connected, and the optical signal propagated through the optical sensor unit is changed in each optical sensor chip depending on the state of the specimen. As a result, since the state of the specimen detected by each optical sensor chip can be specified by analyzing the change in the optical signal depending on the state of the specimen, the optical sensor chip according to the present disclosure can be used to collectively measure the state of a plurality of portions of the specimen.

DESCRIPTION OF EMBODIMENTS

First Embodiment

Figure 1:
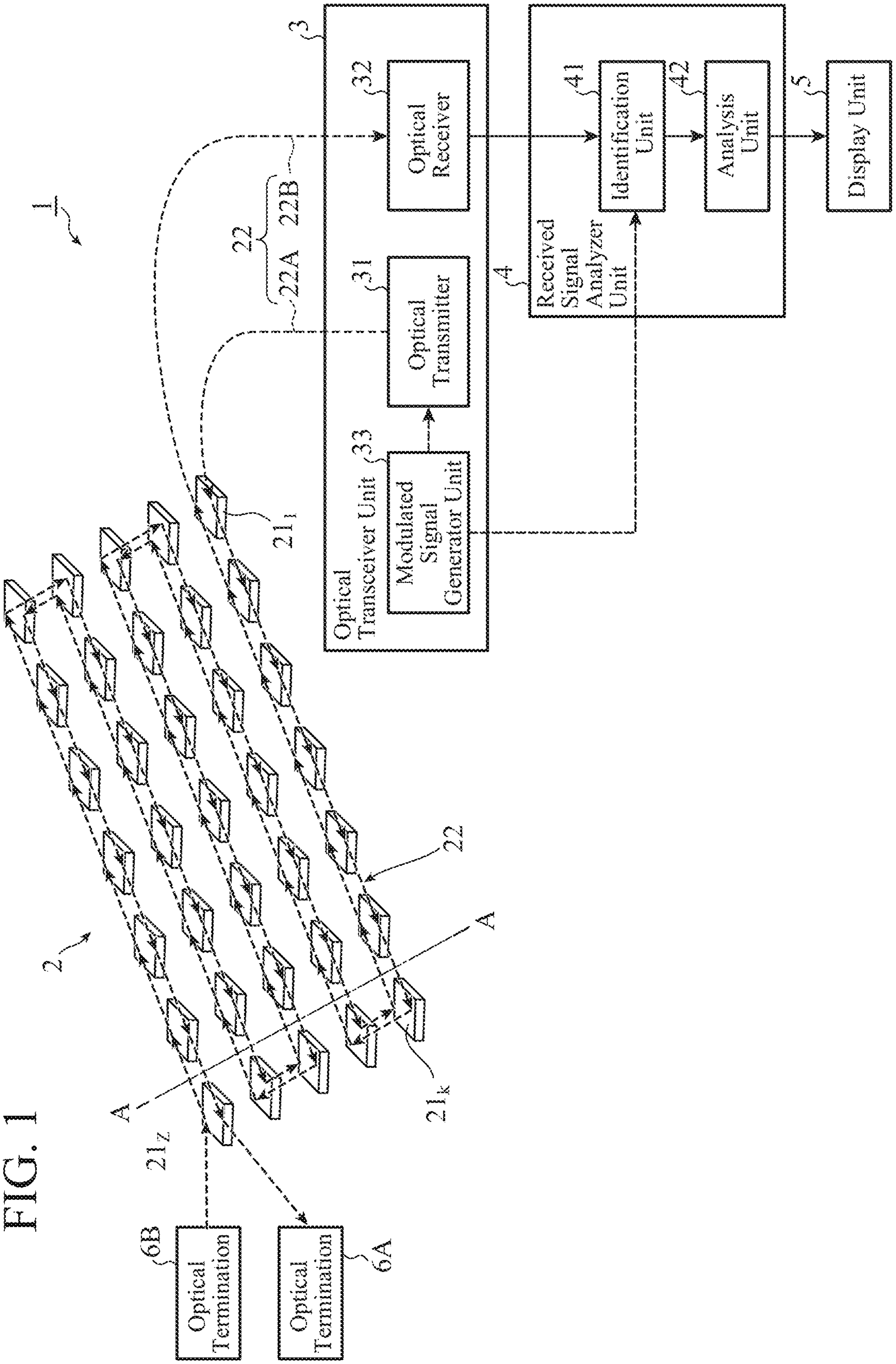
FIG. 1 is a configuration diagram illustrating an optical sensor system according to a first embodiment.

FIG. 1 is a configuration diagram illustrating an optical sensor system 1 according to a first embodiment. In FIG. 1, the optical sensor system 1 is a system that measures the state of a specimen using an optical sensor unit 2. The optical sensor system 1 measures the state of a solid, liquid, or gas specimen, and the specimen may be a living body such as a human or an animal. In addition, the state of the specimen is a state where measurement by Z optical sensor chips $\mathbf{21}_k$ included in the optical sensor unit 2 can be performed, and also includes a state inside the specimen or a state around the specimen. The state of the specimen is, for example, a temperature inside or around the specimen, a moisture content of the specimen, or a pressure applied from the specimen.

The optical sensor unit 2 includes Z optical sensor chips $\mathbf{21}_k$ each connected by an optical fiber 22. k is any natural number equal to or larger than 1 and equal to or less than Z. For example, as illustrated in FIG. 1, the Z optical sensor chips $\mathbf{21}_k$ are a unit in which optical sensor chips from an optical sensor chip $\mathbf{21}_1$ to an optical sensor chip $\mathbf{21}_Z$ are continuously arranged and wired by a transmission-side optical fiber 22A and a reception-side optical fiber 22B. The specimen is disposed in contact with the optical sensor chips $\mathbf{21}_k$ of the optical sensor unit 2 or disposed in a non-contact manner in the vicinity thereof.

In the optical sensor unit 2, the connection form of the Z optical sensor chips $\mathbf{21}_k$ is not limited to that illustrated in FIG. 1, and a free connection form is possible. For example, a plurality of optical sensor chips $\mathbf{21}_k$ may be connected together, and one of the optical sensor chips $\mathbf{21}_k$ and an optical transceiver unit 3 may be connected. The Z optical sensor chips $\mathbf{21}_k$ may be connected to the optical transceiver unit 3 directly or via another optical sensor chip $\mathbf{21}_k$.

The optical sensor system 1 may be a device in which Z optical sensor chips $\mathbf{21}_k$ from the optical sensor chip $\mathbf{21}_1$ to the optical sensor chip $\mathbf{21}_Z$ are continuously provided via the optical fiber 22 on the surface of the specimen or the surface on which the specimen is disposed. Since an optical signal is input and output between the optical sensor chip $\mathbf{21}_k$ and an optical sensor chip $\mathbf{21}_{k-1}$ through the optical fibers 22A and 22B, it is possible to detect the state of the specimen without using an electric signal for a specimen-state detection signal and without providing a sensor circuit unit for each optical sensor chip.

The optical fiber 22 includes the transmission-side optical fiber 22A and the reception-side optical fiber 22B. Note that the optical fiber 22 may be one optical fiber having both functions of the transmission side and the reception side. Among the Z optical sensor chips $\mathbf{21}_k$ in the optical sensor unit 2, the optical sensor chip $\mathbf{21}_1$ at one end portion is connected to an optical transmitter unit 31 via the optical fiber 22A and connected to an optical receiver unit 32 via the optical fiber 22B. The optical sensor chip $\mathbf{21}_Z$ at the other end portion is connected to an optical termination 6A via the optical fiber 22A and connected to an optical termination 6B via the optical fiber 22B.

The optical transceiver unit 3 includes the optical transmitter unit 31, the optical receiver unit 32, and a modulated signal generator unit 33. The optical transmitter unit 31 transmits a first optical signal to the optical sensor chip $\mathbf{21}_1$ through the optical fiber 22A. The modulated signal generator unit 33 generates an electrical modulation signal with a predetermined modulation scheme for modulating light emitted from a light emitting element as a light source, and outputs the electrical modulation signal to the optical transmitter unit 31 and an identification unit 41. The optical transmitter unit 31 outputs a first optical signal obtained by modulating the light emitted from the light emitting element on the basis of the electrical modulation signal to the optical fiber 22A connected to the optical sensor chip $\mathbf{21}_1$.

The modulated signal generated by the modulated signal generator unit 33 is only required to be a modulated signal capable of measuring the reciprocating time of a propagated signal, and for example, a pulse modulated signal, a frequency modulated signal, or a phase modulated signal may be used. The first optical signal generated by the optical transmitter unit 31 is, for example, an optical signal with one predetermined wavelength, and an electrical signal in which one of an intensity characteristic, a phase characteristic, and a frequency characteristic is modulated is applied. The value of one predetermined wavelength is a design value of the resonance wavelength of a changer unit 213. As long as the first optical signal includes a wavelength corresponding to the design value of the resonance wavelength of the changer unit 213, the first optical signal may be an optical signal having a plurality of wavelengths, that is, an optical signal in which a plurality of wavelengths are multiplexed.

Note that in a case where the first optical signal is not modulated, the optical transceiver unit 3 does not need to include the modulated signal generator unit 33.

The optical receiver unit 32 receives a second optical signal from the optical sensor chip $\mathbf{21}_1$ through the optical fiber 22B. The optical receiver unit 32 includes a light receiving element, and the light receiving element converts the received second optical signal into an electrical signal. The light emitting element and the light receiving element may be provided separately, or may be an optical sensor in which the light emitting element and the light receiving element are integrated into one. The optical transceiver unit 3 may be provided separately from the optical sensor unit 2, or may be provided in the optical sensor unit 2. For example, the optical transceiver unit 3 may be integrated on an InP substrate provided in a part of the optical sensor unit 2.

In the optical sensor chip $\mathbf{21}_Z$, the optical termination 6A is a portion provided at the end portion of the optical fiber 22A in such a manner as to minimize light reflection. The first optical signal sequentially propagated from the optical sensor chip $\mathbf{21}_1$ to the optical sensor chip $\mathbf{21}_Z$ is terminated at the optical termination 6A. In addition, in the optical sensor chip $\mathbf{21}_Z$, the optical termination 6B is a portion provided at the end portion of the optical fiber 22B in such a manner as to minimize light reflection. The second optical signal is terminated at the optical termination 6B. The optical terminations 6A and 6B may be one optical termination for both transmission and reception.

A received signal analyzer unit 4 measures the state of the specimen disposed in the optical sensor unit 2 by analyzing a received signal of the second optical signal received by the optical receiver unit 32. In addition, the received signal analyzer unit 4 includes the identification unit 41 and an analysis unit 42.

The identification unit 41 identifies each of the optical sensor chips 21$_k$ using the received signal of the second optical signal. For example, the identification unit 41 detects the received signal of the second optical signal on the basis of the electrical modulation signal generated by the modulated signal generator unit 33 and reads the wavelength value thereof, thereby specifying the identification number k of the modulated optical sensor chip 21$_k$. As a result, the identification unit 41 identifies each of the optical sensor chips 21$_k$.

The analysis unit 42 specifies the state of the specimen disposed in the optical sensor unit 2 for each optical sensor chip 21$_k$ by analyzing the received signal of the second optical signal. For example, the analysis unit 42 reads the intensity difference of the received signal for each optical sensor chip 21$_k$ identified using the identification number k of the optical sensor chip 21$_k$, thereby specifying the state of the specimen around the optical sensor chips 21$_k$. A display unit 5 receives measurement results of the state of the specimen from the received signal analyzer unit 4, and displays the received measurement results.

Figure 2A:
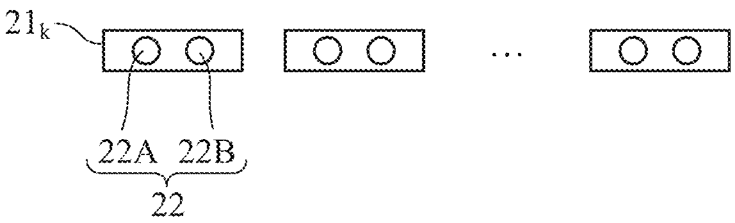
FIG. 2A is a cross-sectional arrow view illustrating a cross-section of an optical sensor unit taken along line A-A in FIG. 1.
Figure 2B:
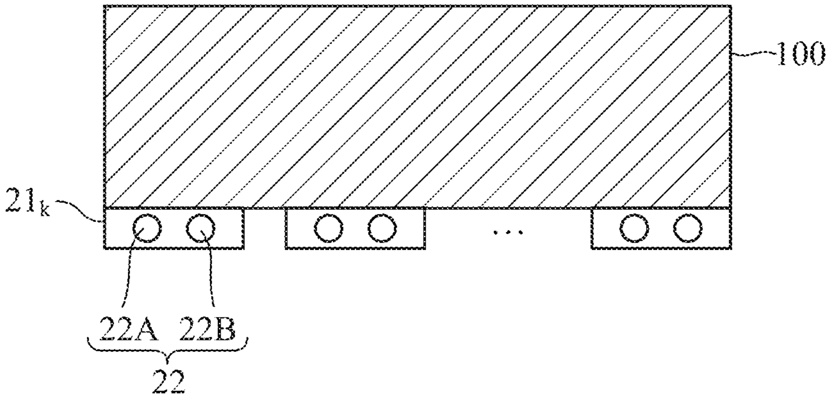
FIG. 2B is a cross-sectional arrow view illustrating a cross-section of the optical sensor unit in which a specimen is disposed taken along line A-A.

FIG. 2A is a cross-sectional arrow view illustrating a cross-section of the optical sensor unit 2 taken along line A-A in FIG. 1. FIG. 2B is a cross-sectional arrow view illustrating a cross-section of the optical sensor unit 2 in which a specimen 100 is disposed taken along line A-A. As illustrated in FIGS. 2A and 2B, in the optical sensor unit 2, the optical sensor chips 21$_k$ adjacent to each other in the direction in which a plurality of optical sensor chips 21$_k$ are continuous are connected by the optical fiber 22A and the optical fiber 22B.

As illustrated in FIG. 2B, the specimen 100 is disposed on the optical sensor chips 21$_k$ in the optical sensor unit 2. The optical sensor chip 21$_k$ includes, for example, an optical waveguide manufactured using microfabrication technology represented by silicon photonics technology. The optical sensor chip 21$_k$ changes at least one of the intensity, the phase, or the frequency of the first optical signal depending on the state of the specimen 100.

Figure 3:
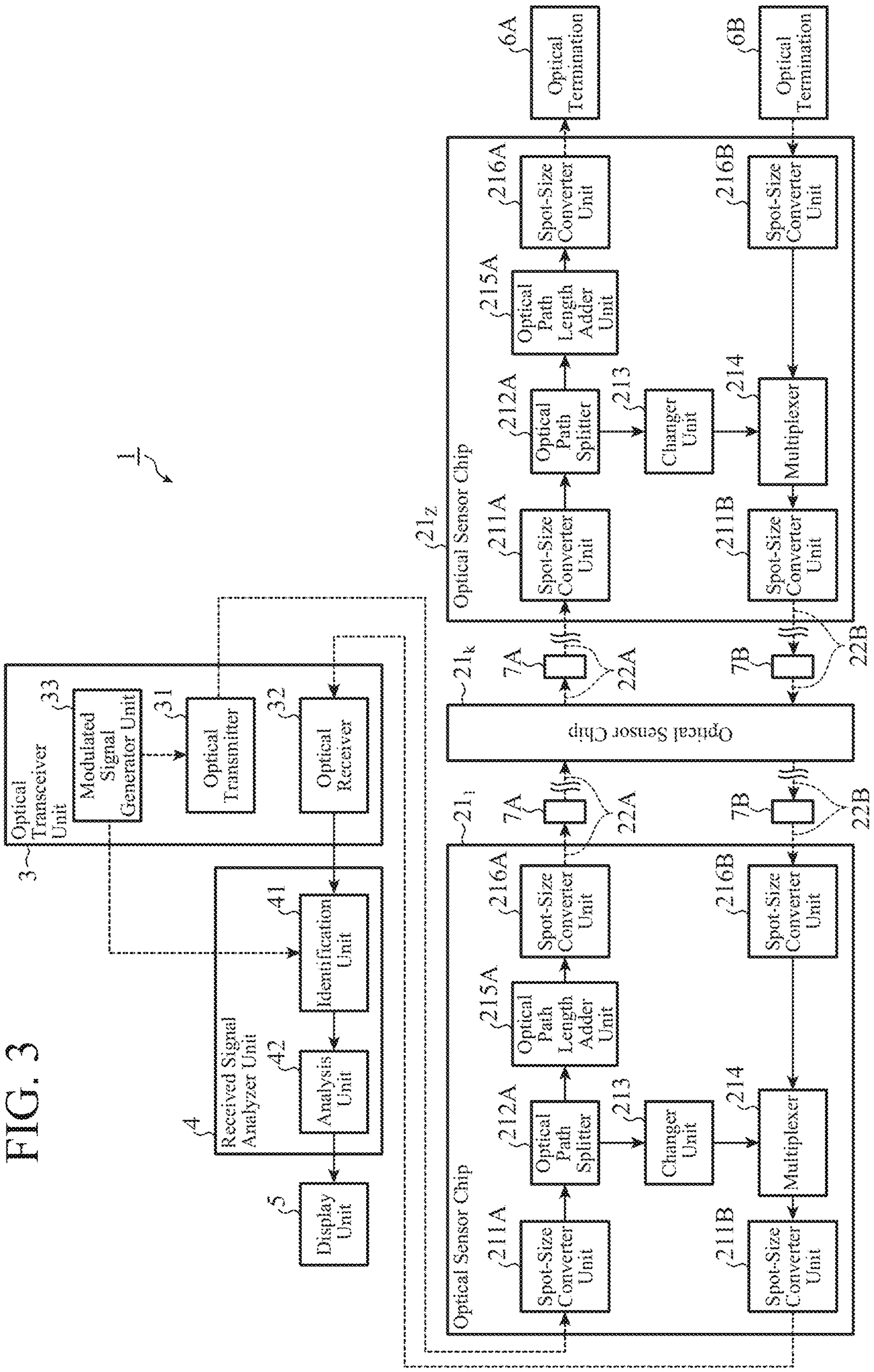
FIG. 3 is a configuration diagram specifically illustrating the optical sensor system according to the first embodiment.

FIG. 3 is a configuration diagram specifically illustrating the optical sensor system 1. In FIG. 3, the optical sensor unit 2 is configured by continuously connecting Z optical sensor chips 21$_k$. Each of the optical sensor chip 21$_1$ to an optical sensor chip 21$_{Z-1}$ includes a spot-size conversion unit 211A, a spot-size conversion unit 211B, an optical path splitter unit 212A, the changer unit 213, a multiplexer unit 214, an optical path length adder unit 215A, a spot-size conversion unit 216A, and a spot-size conversion unit 216B.

The spot-size conversion units 211A, 211B, 216A, and 216B are optical elements that convert the spot size, which is the magnitude of the spread of the light distribution in the optical fiber, and the spot size in the waveguide. The spot-size conversion units 211A, 211B, 216A, and 216B are, for example, a spot size converter including a waveguide. The waveguide is, for example, a silicon waveguide.

The spot-size conversion unit 211A converts the spot size of the first optical signal propagated through the optical fiber 22A from the optical transmitter unit 31 or the optical sensor chip 21$_{k-1}$ disposed at a preceding stage based on the waveguide inside the optical sensor chip 21$_k$. The spot-size conversion unit 211A is an example of a first interface unit included in the optical sensor chip 21$_k$.

Note that the optical sensor chip 21$_k$ may receive the first optical signal without converting the spot size of the first optical signal. For example, the optical sensor chip 21$_k$ may have a configuration in which the optical fiber 22A and the waveguide inside the chip are connected without the spot-size conversion unit 211A. In this case, the first interface unit is a connection point of the waveguide inside the chip and the optical fiber 22A.

The spot-size conversion unit 216A converts the spot size of the first optical signal based on the optical fiber 22A, and outputs the first optical signal with the converted spot size to the optical fiber 22A. The spot-size conversion unit 216A is an example of a second interface unit included in the optical sensor chip 21$_k$.

Note that the optical sensor chip 21$_k$ may output the first optical signal without converting the spot size of the first optical signal. For example, the optical sensor chip 21$_k$ may have a configuration in which the waveguide inside the chip and the optical fiber 22A are connected without the spot-size conversion unit 216A. In this case, the second interface unit is a connection point of the waveguide inside the chip and the optical fiber 22A. For example, in the optical sensor chip 21$_k$, by adding an optical path length to a path through which the first optical signal propagates, the first optical signal propagates with a predetermined delay time.

Furthermore, in the optical sensor system 1, even if each of the optical sensor chips 21$_k$ does not have the optical path length adder unit 215A, a delay corresponding to the optical path inside each of the optical sensor chips 21$_k$ occurs in the first optical signal propagated from the optical sensor chip 21$_1$ to the optical sensor chip 21$_Z$. By analyzing these delay times, it is possible to specify the optical signal propagated through each optical sensor chip 21$_k$.

The spot-size conversion unit 216B converts the spot size of the second optical signal propagated through the optical fiber 22B from the optical sensor chip 21-+1 disposed at a subsequent stage based on the waveguide inside the optical sensor chip 21$_k$, and outputs the second optical signal with the converted spot size to the inside of the optical sensor chip 21$_k$. The spot-size conversion unit 216B is an example of a third interface unit included in the optical sensor chip 21$_k$.

Note that the optical sensor chip 21$_k$ may receive the second optical signal without converting the spot size of the second optical signal. For example, the optical sensor chip 21$_k$ may have a configuration in which the optical fiber 22B and the waveguide inside the chip are connected without the spot-size conversion unit 216B. In this case, the third interface unit is a connection point of the waveguide inside the chip and the optical fiber 22B.

The spot-size conversion unit 211B converts the spot size of an optical signal in which the first optical signal changed depending on the state of the specimen and the second optical signal are multiplexed based on the optical fiber 22B, and outputs the optical signal with the converted spot size to the optical fiber 22B. The spot-size conversion unit 211B is an example of a fourth interface unit included in the optical sensor chip 21$_k$.

Note that the optical sensor chip 21$_k$ may output the optical signal without converting the spot size of the optical signal. For example, the optical sensor chip 21$_k$ may have a configuration in which the waveguide inside the chip and the optical fiber 22B are connected without the spot-size conversion unit 211B. In this case, the fourth interface unit is a connection point of the optical fiber 22B and the waveguide inside the chip.

The optical path splitter unit 212A splits the input first optical signal to the changer unit 213 and the optical path length adder unit 215A. Here, since the optical sensor system 1 analyzes the delay of the first optical signal to identify the individual optical sensor chips $21_k$, when the optical path splitter unit 212A receives the first optical signal with a single wavelength, a part of the input first optical signal is split to the changer unit 213, and the remaining part of the input first optical signal is split to the optical path length adder unit 215A. Note that the split ratio is not limited.

Furthermore, in a case where the optical sensor system 1 analyzes the wavelength of the first optical signal to identify the individual optical sensor chips $21_k$, an optical path splitter unit that selects a signal component with a predetermined wavelength from the first optical signal with a plurality of wavelengths and outputs the signal component to the changer unit 213 may be used as the optical path splitter unit 212A. For example, the optical path splitter unit 212A splits the first optical signal with a plurality of wavelengths to the optical path length adder unit 215A, selects the first optical signal with a wavelength value corresponding to the design value of the resonance wavelength of the changer unit 213 among the plurality of wavelength values of the first optical signal, and splits the selected first optical signal to the changer unit 213.

The changer unit 213 changes the characteristics of the first optical signal input to the optical sensor chip $21_k$ depending on the state of the specimen 100. The characteristics of the first optical signal include an intensity characteristic, a phase characteristic, or a frequency characteristic. The changer unit 213 changes at least one of the intensity characteristic, the phase characteristic, or the frequency characteristic of the first optical signal.

For example, the changer unit 213 is implemented by a ring resonator that is an optical waveguide. Note that the changer unit 213 is only required to change the characteristics of the first optical signal depending on the state of the specimen 100, and may be a phase shifter including an optical waveguide, a frequency shifter including an optical waveguide, or an optical element including a combination of the phase shifter and the frequency shifter. Furthermore, the changer unit 213 may be a ring resonator, a Mach-Zehnder interferometer (MZI), or a combination thereof.

Even the changer unit 213 with these configurations can change the characteristics of the first optical signal depending on the state of the specimen 100.

The first optical signal changed depending on the state of the specimen in the changer unit 213 may be output from the spot-size conversion unit 216A. In this case, the optical sensor chip $21_{k+1}$ adjacent to the optical sensor chip $21_k$ further changes the first optical signal, which has been changed by the changer unit 213 of the optical sensor chip $21_k$ depending on the state of the specimen 100, by the changer unit 213 of the optical sensor chip $21_{k-1}$ depending on the state of the specimen 100. Therefore, it is necessary for the received signal analyzer unit 4 to take into consideration that the signal is affected by a plurality of changer units 213.

The plurality of changer units 213 may be provided in one optical sensor chip $21_k$. In this case, the plurality of changer units 213 may change the characteristics of the first optical signal depending on mutually different states of the specimen 100. For example, a sensor group in which a plurality of changer units 213 are connected in series is provided in one optical sensor chip $21_k$. Among the plurality of changer units 213 connected in series, a certain changer unit 213 changes the characteristics of the first optical signal depending on the temperature of the specimen 100, another changer unit 213 changes the characteristics of the first optical signal depending on the moisture content of the specimen 100, and still another changer unit 213 changes the characteristics of the first optical signal depending on the pressure applied from the specimen 100.

The multiplexer unit 214 multiplexes the first optical signal changed depending on the state of the specimen 100 and the second optical signal input by the spot-size conversion unit 216B. The optical signal in which the first optical signal changed by the changer unit 213 and the second optical signal are multiplexed is output to the spot-size conversion unit 211B. The spot-size conversion unit 211B included in the optical sensor chip $21_k$ outputs the optical signal multiplexed by the multiplexer unit 214 to the optical sensor chip $21_{k-1}$ as the second optical signal.

The optical path length adder unit 215A is a first optical path length adder unit that is an optical path with an optical path length for delaying the first optical signal. For example, the optical path length adder unit 215A included in the optical sensor chip $21_k$ delays the relative propagation time of the first optical signal input from the optical sensor chip $21_{k-1}$ by adding the optical path length to the optical path of the first optical signal, and outputs the resultant first optical signal to the spot-size conversion unit 216A as the first optical signal to be output to the optical sensor chip $21_{k+1}$.

Note that the optical path length adder unit 215A may be provided not in the optical sensor chip $21_k$ but in the optical fiber 22A connecting the optical sensor chip $21_k$ and the optical sensor chip $21_{k+1}$. In this case, for example, the optical path length adder unit 215A may be obtained by processing the optical fiber 22A in such a manner that the optical signal is delayed.

In the optical sensor chip $21_k$, waveguides optically connecting the spot-size conversion unit 211A and the optical path splitter unit 212A, the optical path splitter unit 212A and the changer unit 213, the optical path splitter unit 212A and the optical path length adder unit 215A, the changer unit 213 and the multiplexer unit 214, and the optical path length adder unit 215A and the spot-size conversion unit 216A propagate the first optical signal whose spot size has been converted by the spot-size conversion unit 211A. Waveguides optically connecting the spot-size conversion unit 216B and the multiplexer unit 214, and the multiplexer unit 214 and the spot-size conversion unit 211B propagate the second optical signal whose spot size has been converted by the spot-size conversion unit 216B.

A connector 7A is an optical connector that optically connects the optical fiber 22A connected to the spot-size conversion unit 216A included in the optical sensor chip $21_k$ and the optical fiber 22A connected to the spot-size conversion unit 211A included in the optical sensor chip $21_{k+1}$ adjacent to the optical sensor chip $21_k$. In addition, a connector 7B is an optical connector that optically connects the optical fiber 22B connected to the spot-size conversion unit 211B included in the optical sensor chip $21_{k+1}$ and the optical fiber 22B connected to the spot-size conversion unit 216B included in the optical sensor chip $21_k$ adjacent to the optical sensor chip $21_{k+1}$.

In the optical sensor chip $21_k$, the spot-size conversion unit 211A and the spot-size conversion unit 211B may constitute one interface unit, and the spot-size conversion unit 216A and the spot-size conversion unit 216B may constitute one interface unit.

For example, the connector 7A and the connector 7B are formed as one optical connector, and this optical connector is shared by the optical fiber 22A and the optical fiber 22B. As a result, the spot-size conversion unit 211A and the spot-size conversion unit 211B form one interface unit, and the spot-size conversion unit 216A and the spot-size conversion unit 216B form one interface unit.

With this configuration, the number of components for installing the optical sensor chip $21_k$ is reduced, and the installation work is also simplified.

Figure 4:
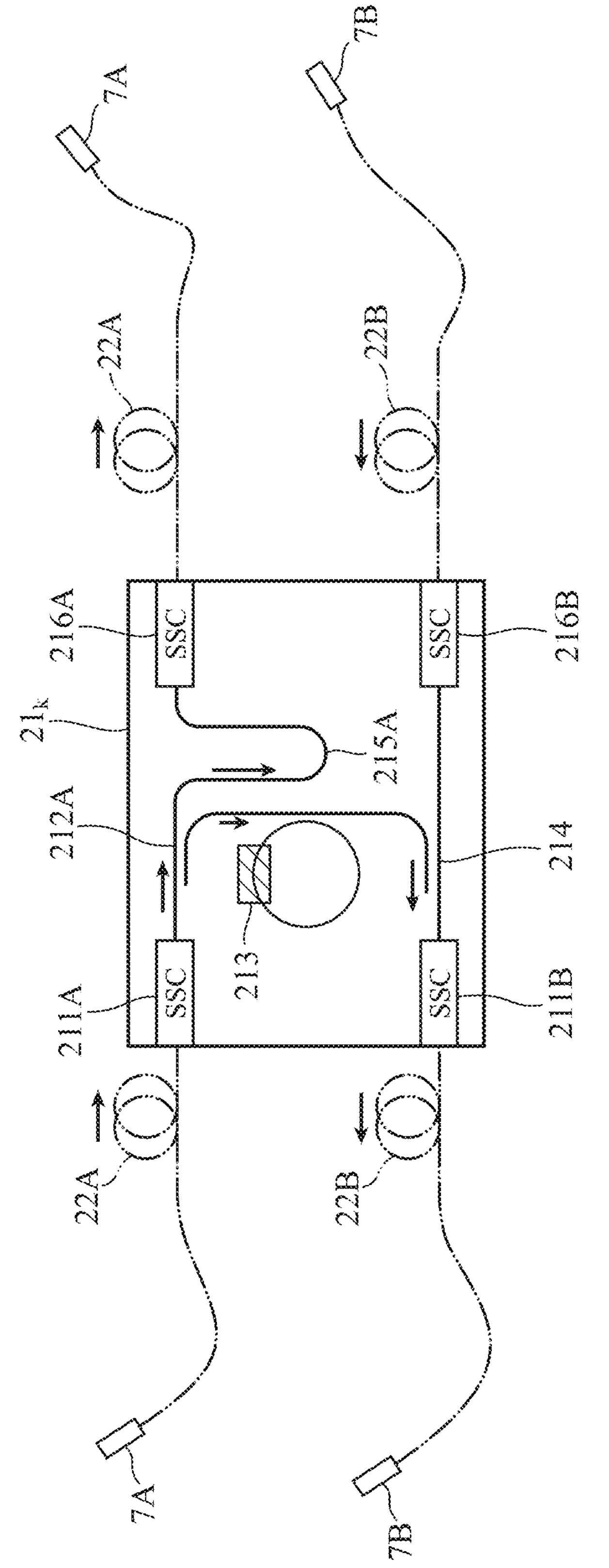
FIG. 4 is a configuration diagram specifically illustrating an optical sensor chip and an optical waveguide according to the first embodiment.

FIG. 4 is a configuration diagram specifically illustrating the optical sensor chip $21_k$ and an optical waveguide. In FIG. 4, the spot-size conversion units 211A, 211B, 216A, and 216B are Spot-Size-Converters (SSC). Multi-Mode Interference (MMI) couplers or directionally couplers can be used as the optical path splitter unit 212A and the multiplexer unit 214. A ring resonator, a phase shifter, a frequency shifter, or an optical element obtained by combining these can be used as the changer unit 213. A waveguide delay optical circuit can be used as the optical path length adder unit 215A. The optical fibers 22A and 22B can be replaced by optical waveguides.

Figure 5:
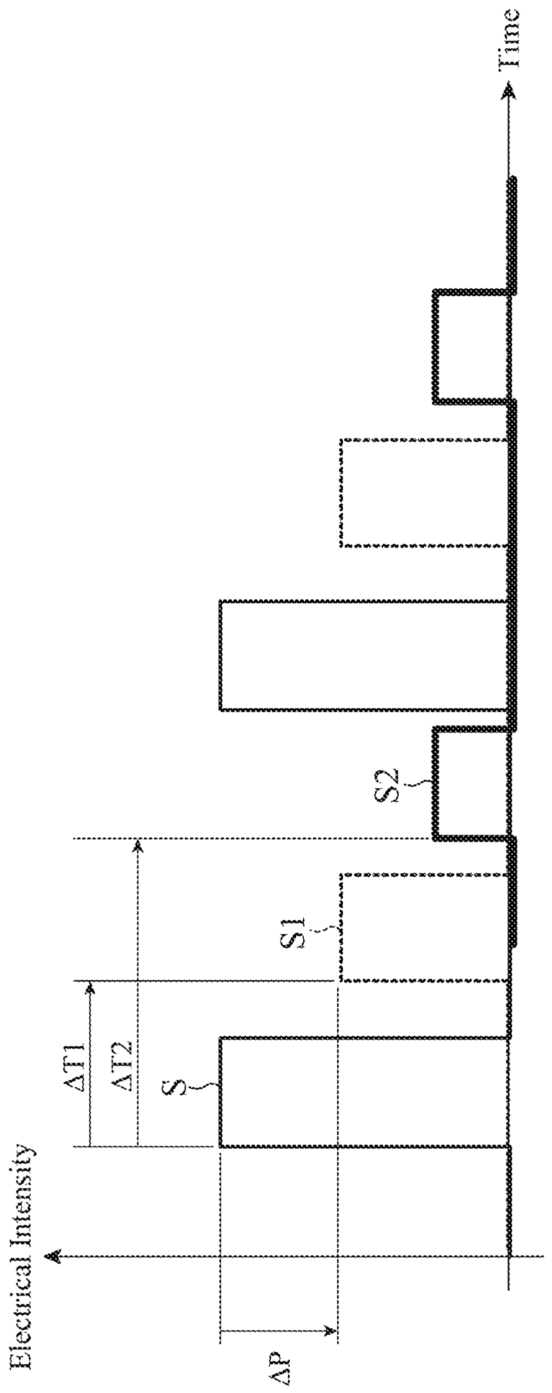
FIG. 5 is a waveform diagram illustrating time waveforms of a first optical signal before transmission and a received signal of a second optical signal in the optical sensor system according to the first embodiment.

FIG. 5 is a waveform diagram illustrating a time waveform of a first optical signal S before transmission and time waveforms of received signals S1 and S2 that are optical signals received by the optical receiver unit 32 in the optical sensor system 1, and the first optical signal S is a pulse signal. The modulated signal generator unit 33 generates a pulse modulated signal and applies the pulse modulated signal to the optical transmitter unit 31, so that the first optical signal S illustrated in FIG. 5 is generated. The first optical signal S propagates from the optical sensor chip $21_1$ to the optical sensor chip $21_Z$ in the optical sensor unit 2, so that the processing of identifying the optical sensor chip $21_k$ is performed, and the characteristics are changed depending on the state of the specimen 100.

In the optical sensor chip $21_Z$, the optical path splitter unit 212A splits the first optical signal input by the spot-size conversion unit 211A to the changer unit 213 and the optical path length adder unit 215A. The first optical signal propagated through the optical path length adder unit 215A and the spot-size conversion unit 216A is terminated by the optical termination 6A connected to the optical sensor chip $21_Z$.

On the other hand, the changer unit 213 changes the first optical signal depending on the state of the specimen 100. The multiplexer unit 214 outputs an optical signal in which the first optical signal based on the state of the specimen 100 and the second optical signal input by the spot-size conversion unit 216B are multiplexed to the spot-size conversion unit 211B. The spot-size conversion unit 211B outputs the multiplexed signal whose spot size has been converted based on the optical fiber 22B to the optical sensor chip $21_{Z-1}$ as the second optical signal.

In FIG. 5, the processing of identifying the optical sensor chip $21_k$ is processing of adding an optical path length to the optical path of the first optical signal. In each optical sensor chip $21_k$, the first optical signal is delayed by the propagation time corresponding to the optical path length added by the optical path length adder unit 215A. As a result, a time difference due to the delay in each optical sensor chip $21_k$ occurs in the second optical signal output from the optical sensor chip $21_1$.

For example, as illustrated in FIG. 5, a time difference ΔT1 from the original first optical signal S occurs in the received signal S1, and a time difference ΔT2 from the original first optical signal S occurs in the received signal S2. By analyzing the time difference ΔT1 in the received signal S1 and the time difference ΔT2 in the received signal S2 from the original first optical signal S, the identification unit 41 can identify the optical sensor chip that has output the received signal S1 and the optical sensor chip that has output the received signal S2. The identification unit 41 associates an identification number k predetermined in the optical sensor chip $21_k$ with each of the received signals S1 and S2.

In addition, in the optical sensor system 1, even if each optical sensor chip $21_k$ does not have the optical path length adder unit 215A, a delay based on the optical path inside the chip occurs. By analyzing these delay times, it is possible to specify the optical signal propagated through each optical sensor chip $21_k$. A delay based on the optical path inside each optical sensor chip $21_k$ occurs in the first optical signal propagated from the optical sensor chip $21_1$ to the optical sensor chip $21_Z$. By analyzing these delay times, it is possible to specify the optical signal propagated through each optical sensor chip $21_k$.

The first optical signal may be phase-modulated or frequency-modulated. For example, the modulated signal generator unit 33 generates a frequency modulated signal and applies the frequency modulated signal to the optical transmitter unit 31, so that a frequency-modulated first optical signal is generated. By transmitting the first optical signal to the optical sensor chip $21_1$, the optical receiver unit 32 receives the frequency-modulated optical signal. The optical receiver unit 32 performs heterodyne detection on the received signal and specifies the amount of frequency shift of each received signal.

The first optical signal S multiplexed with the received signal S1 and the received signal S2 changes depending on the state of the specimen 100. In the example illustrated in FIG. 5, the intensity of the first optical signal decreases depending on the state of the specimen 100, and thus an intensity difference ΔP from the original first optical signal S occurs in the received signal S1, and a larger intensity difference than that of the received signal S1 occurs in the received signal S2. When the identification unit 41 identifies the optical sensor chip $21_k$, the analysis unit 42 specifies the state of the specimen 100 in each optical sensor chip $21_k$ by analyzing the intensity difference between the received signals S1 and S2 and the first optical signal S. The method of analyzing a received signal is not limited to the intensity analysis of the received signal, and may be analysis of a phase characteristic or a frequency characteristic.

Next, a measurement method according to the first embodiment will be described.

Figure 6:
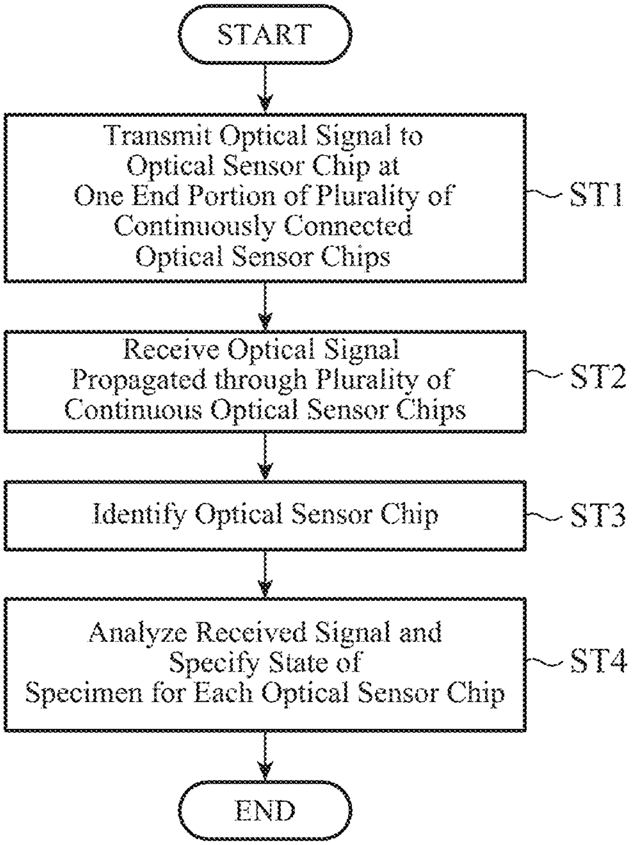
FIG. 6 is a flowchart illustrating a measurement method according to the first embodiment.

FIG. 6 is a flowchart illustrating the measurement method according to the first embodiment, and illustrates an operation of the optical sensor system 1. The optical transmitter unit 31 transmits a first optical signal to the optical sensor chip $21_1$ in the optical sensor unit 2 in which the specimen 100 is disposed (step ST1). For example, the optical transmitter unit 31 transmits the first optical signal to the optical sensor chip $21_1$ at one end portion of the optical sensor unit 2 in which a plurality of optical sensor chips $21_k$ are continuously connected.

Next, the optical receiver unit 32 receives an optical signal propagated through the plurality of continuous optical sensor chips $21_k$ from the optical sensor chip $21_1$ (step ST2). The optical receiver unit 32 generates a received signal from the received optical signal and outputs the received signal to the identification unit 41. By analyzing the received signal, the identification unit 41 identifies the optical sensor chip $21_k$ corresponding to the received signal (step ST3). Thereafter, by analyzing the received signal for each of the optical sensor chips $21_k$ identified by the identification unit 41, the analysis unit 42 specifies the state of the specimen 100 for each of the optical sensor chips $21_1$ (step ST4).

Figure 7:
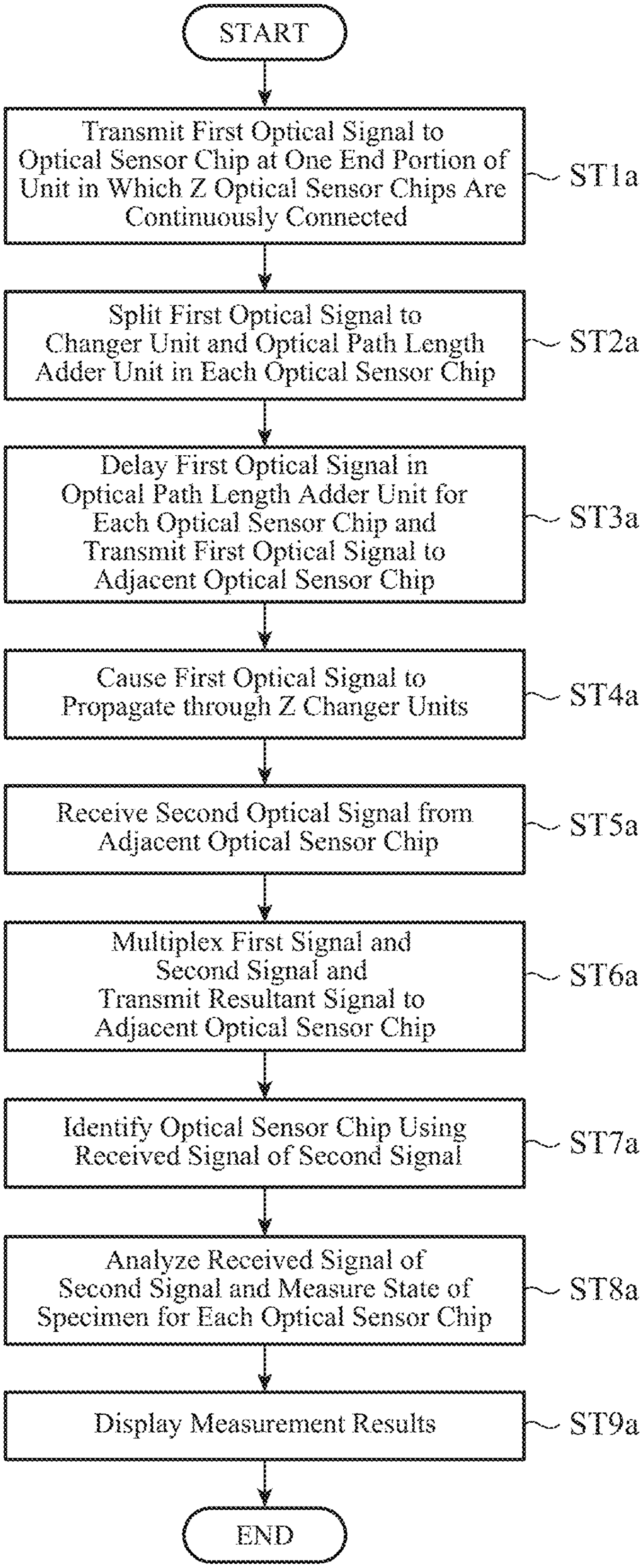
FIG. 7 is a flowchart illustrating a flow of an optical signal in the optical sensor unit.

FIG. 7 is a flowchart illustrating a flow of an optical signal in the optical sensor unit 2, and it is assumed that Z optical sensor chips $21_k$ are continuously connected in the optical sensor unit 2. The specimen 100 is disposed in the optical sensor unit 2. The optical transmitter unit 31 generates a first optical signal using light emitted from a light source and transmits the first optical signal to the optical sensor chip $21_1$ at one end portion of the optical sensor unit 2 (step ST1a).

In a case where moisture contained in the specimen 100 is detected, a wavelength in the absorption wavelength band of water is set as the resonance wavelength of the changer unit 213 included in each of the Z optical sensor chips $21_k$. The optical transmitter unit 31 transmits a first optical signal in which Z wavelengths set in the changer units 213 of the Z optical sensor chips $21_k$ are multiplexed to the optical sensor chip $21_1$. As a result, the first optical signal propagates from the optical sensor chip $21_1$ to the optical sensor chip $21_Z$.

The optical path splitter unit 212A in each optical sensor chip $21_k$ splits the first optical signal to the changer unit 213 and the optical path length adder unit 215A (step ST2a). In the optical sensor chip $21_k$, the optical path length adder unit 215A delays the first optical signal by adding the optical path length thereto and outputs the resultant first optical signal to the optical sensor chip $21_{k+1}$ (step ST3a). As a result, the first optical signal propagates from the optical sensor chip $21_1$ to the optical sensor chip $21_Z$ while a delay time is added in each optical sensor chip.

In the optical sensor unit 2, the first optical signal propagates through each of the Z changer units 213 (step ST4a). The changer unit 213 changes the first optical signal depending on the state of the specimen 100 and outputs the first optical signal to the multiplexer unit 214. The spot-size conversion unit 216B included in the optical sensor chip $21_k$ receives a second optical signal from the optical sensor chip $21_{k+1}$ and outputs the second optical signal to the multiplexer unit 214 (step ST5a).

While the first optical signal is propagating through the optical sensor unit 2, the changer unit 213 changes the characteristics of the first optical signal depending on the state of the specimen 100. For example, in the changer unit 213 in which the absorption wavelength band of water is set as the resonance wavelength, among wavelength components of the wavelength multiplexed first optical signal, the wavelength component in the absorption wavelength band of water is absorbed by the moisture of the specimen 100, and the intensity of the first optical signal decreases.

In the optical sensor unit 2, the first optical signal changed depending on the state of the specimen 100 and the second optical signal that is the optical signal input by the spot-size conversion unit 216B propagate through each of the Z multiplexer units 214. The multiplexer unit 214 multiplexes the first optical signal changed depending on the state of the specimen 100 and the second optical signal. In the optical sensor chip $21_k$, the spot-size conversion unit 211B outputs the optical signal in which the first optical signal and the second optical signal are multiplexed to the optical sensor chip $21_{k-1}$ (step ST6a).

The optical receiver unit 32 receives the optical signal in which the first optical signal and the second optical signal are multiplexed from the optical sensor chip $21_1$ and outputs the optical signal to the identification unit 41. The identification unit 41 identifies the optical sensor chip $21_k$ corresponding to a received signal using the modulated signal generated by the modulated signal generator unit 33 and the received signal of the optical signal received by the optical receiver unit 32 (step ST7a).

For example, the identification unit 41 calculates the propagation time of the received signal with respect to the first optical signal by comparing the propagation of the pulse of the original first optical signal (the first optical signal before transmission) specified by the modulated signal with the propagation of the pulse of the received signal. In the identification unit 41, the propagation time corresponding to the optical path length added by the optical path length adder unit 215A of each optical sensor chip $21_k$ and the identification number k of the optical sensor chip $21_k$ are registered in association with each other. The identification unit 41 can identify the optical sensor chip $21_k$ corresponding to the received signal by specifying the identification number k corresponding to the propagation time. In addition, the identification unit 41 can also specify the position of the optical sensor chip $21_k$ corresponding to the identification number k.

The analysis unit 42 specifies the state of the specimen 100 for each optical sensor chip $21_k$ by analyzing the received signal (step ST8a). For example, the first optical signal is an optical signal in which a plurality of wavelengths including a wavelength in the absorption wavelength band of water are multiplexed, and the optical sensor chip $21_k$ measures the moisture content of the specimen 100. In this case, in the changer unit 213, among the wavelength components of the first optical signal, the wavelength component in the absorption wavelength band of water is absorbed by the moisture of the specimen 100, and the intensity of the first optical signal decreases.

The analysis unit 42 specifies the moisture content corresponding to the position of the optical sensor chip $21_k$ in the optical sensor unit 2 in which the specimen 100 is disposed using the value of the difference between the intensity of the original first optical signal and the intensity of the received signal. For example, in the analysis unit 42, the relationship between the amount of change in the intensity of the first optical signal and the moisture content is set in advance. The amount of change in the intensity of the first optical signal corresponds to the difference value between the intensity of the first optical signal and the intensity of the received signal. The analysis unit 42 can specify the moisture content of the specimen 100 for each optical sensor chip $21_k$ using the difference value.

The display unit 5 receives measurement results of the state of the specimen 100 from the analysis unit 42, and displays the received measurement results (step ST9a). For example, the analysis unit 42 calculates the two-dimensional distribution of the moisture content of the specimen 100 specified for each optical sensor chip $21_k$, and outputs the two-dimensional distribution to the display unit 5 as the measurement results. As a result, the display unit 5 can graphically display the two-dimensional distribution of the moisture content of the specimen 100.

In the case of detecting the pressure from the specimen 100, a different resonance frequency is set in each of the plurality of optical sensor chips $21_k$. That is, the optical sensor chip $21_k$ is configured to resonate at an individually set frequency. When a pressure is applied from the specimen 100 to the waveguide of the optical sensor chip $21_k$, the waveguide is distorted and resonance conditions change. As a result, the ratio of the optical signal resonated at the frequency set in the optical sensor chip $21_k$ changes. By the analysis unit 42 analyzing the change in the ratio, it is possible to detect the pressure from the specimen 100 for each optical sensor chip $21_k$.

An optical signal in which a plurality of resonance frequencies assigned to the Z optical sensor chips $21_k$ are multiplexed is input to the optical sensor chip $21_1$. The optical signal input to the optical sensor chip $21_1$ sequentially propagates through the plurality of optical sensor chips $21_k$ continuously connected. In the optical sensor chip $21_k$ to which a pressure is applied from the specimen 100, the resonance conditions of the optical signal change. As a result, it is possible to detect the pressure from the specimen 100 for each optical sensor chip $21_k$. In addition, since the analysis unit 42 specifies the position of the optical sensor chip $21_k$ in the optical sensor unit 2, the two-dimensional distribution of the pressure from the specimen 100 can be measured. In this case, the display unit 5 graphically displays the two-dimensional distribution of the pressure from the specimen 100.

Figure 8:
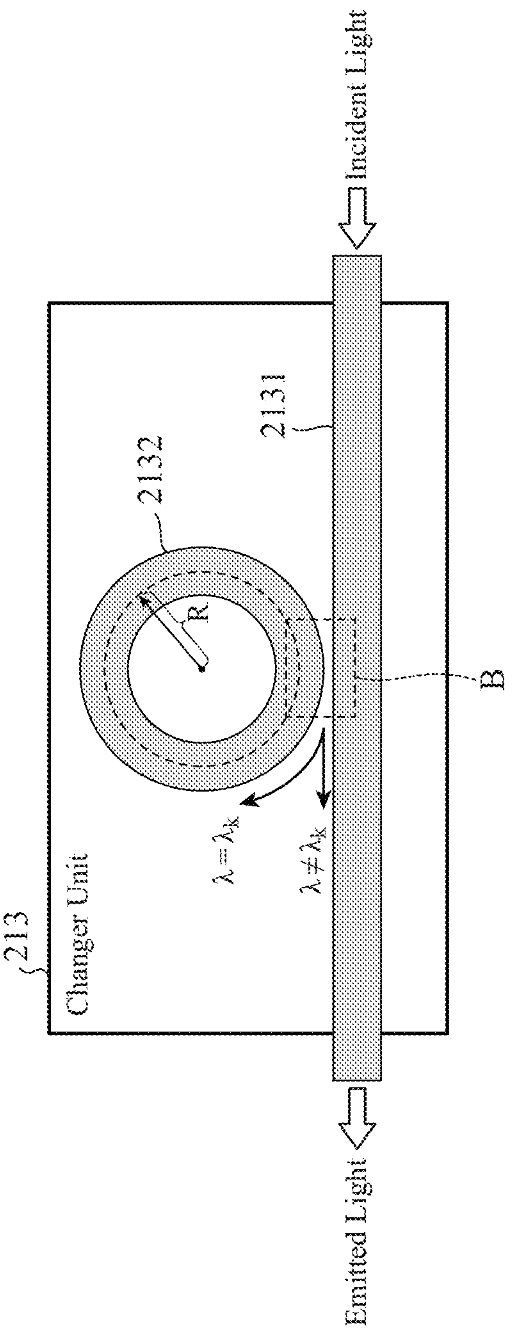
FIG. 8 is a configuration diagram illustrating a changer unit.

FIG. 8 is a configuration diagram illustrating the changer unit 213. The changer unit 213 illustrated in FIG. 8 is a ring resonator. As illustrated in FIG. 8, the ring resonator is a waveguide 2132 with a ring shape. A resonance wavelength based on a curvature radius R and a waveguide effective refractive index $n_{eff}$ of the waveguide 2132 is set in the changer unit 213. The waveguide effective refractive index $n_{eff}$ can be changed by disposing a micro-heater on the waveguide 2131 or stacking a different magnetic body other than silicon.

The changer unit 213 satisfies the relationship of $2\pi \times R \times n_{eff} = m \times \lambda_k$. m is an integer. $\lambda_k$ is a resonance wavelength set in the changer unit 213 included in the optical sensor chip $21_k$. A different resonance wavelength $\lambda_k$ is set in each of the changer units 213 individually included in the Z optical sensor chips $21_k$. The setting of the resonance wavelength $\lambda_k$ means that the waveguide 2132 is configured with the curvature radius R and the waveguide effective refractive index $n_{eff}$ that cause it to resonate at the wavelength $\lambda_k$.

In a case where moisture inside or around the specimen 100 is detected using the optical sensor unit 2, the wavelength $\lambda_k$ in the absorption wavelength band of water is set in the changer unit 213 included in each of the Z optical sensor chips $21_k$. That is, the wavelength $\lambda_1$ is set in the changer unit 213 of the optical sensor chip $21_1$, the wavelength $\lambda_k$ is set in the changer unit 213 of the optical sensor chip $21_k$, and the wavelength $\lambda_Z$ is set in the changer unit 213 of the optical sensor chip $21_Z$.

A region B surrounded by a broken line in FIG. 8 is a region where the waveguide 2131 and the waveguide 2132 are close to each other. Of the first optical signal incident on the changer unit 213, the signal component with the wavelength $\lambda_k$ set in the changer unit 213 propagates through the waveguide 2132 in the region B, and the optical signal component with the wavelength $\lambda$ ($\neq\lambda_k$) other than the wavelength $\lambda_k$ directly propagates through the waveguide 2131 and is emitted from the changer unit 213.

The optical signal with the wavelength $\lambda_k$ resonates while circulating in the waveguide 2132, and is transmitted to the specimen 100 disposed on the waveguide 2132 or to the periphery of the specimen 100 close to the waveguide 2132 during the resonance. In a case where moisture is contained inside the specimen 100 or around the specimen 100, the transmitted optical signal component with the wavelength $\lambda_k$ is absorbed by the water, so that the intensity of the optical signal with the wavelength $\lambda_k$ decreases in proportion to the moisture content. The analysis unit 42 can measure the moisture content of the specimen 100 by analyzing the change in the intensity of the second optical signal.

The case where each optical sensor chip $21_k$ is identified by analyzing the difference in the delay time of the received signal has been described, but each optical sensor chip $21_k$ may be identified by analyzing the difference in the wavelength included in the received signal. In this case, the optical sensor chip $21_k$ does not include the optical path length adder unit 215A in the waveguides of the spot-size conversion unit 211A and the spot-size conversion unit 216A.

Figure 9:
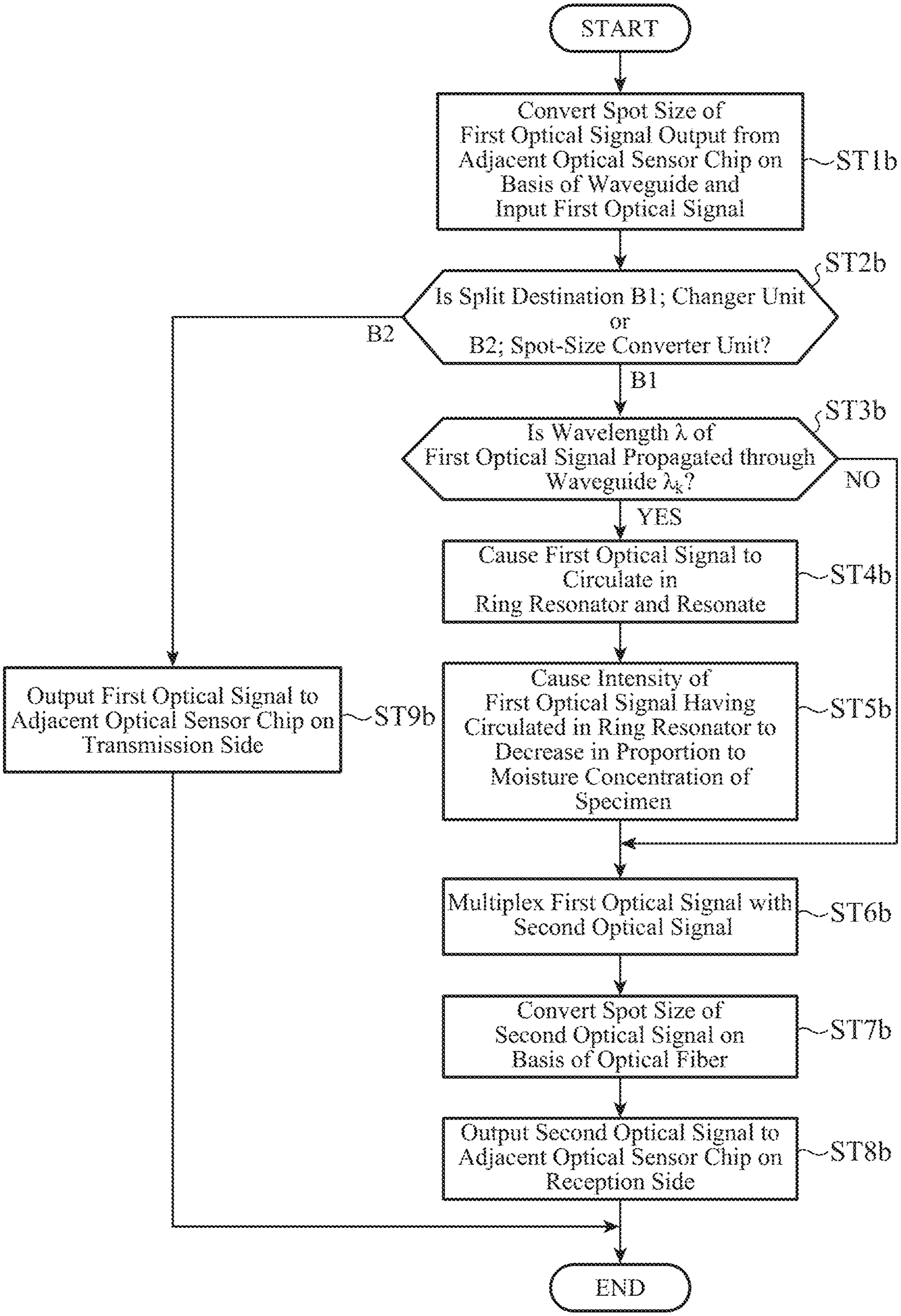
FIG. 9 is a flowchart illustrating an operation of the optical sensor chip.

FIG. 9 is a flowchart illustrating an operation of the optical sensor chip $21_k$, and illustrates a case where the moisture content inside or around the specimen 100 is detected using the optical sensor unit 2 configured by connecting Z optical sensor chips $21_k$. A first optical signal that is continuous light in which the wavelengths $\lambda_1$ to $\lambda_Z$ individually set in the Z optical sensor chips $21_k$ are multiplexed is transmitted to the optical sensor chip $21_1$. The first optical signal transmitted to the optical sensor chip $21_1$ propagates sequentially from the optical sensor chip $21_1$ to the optical sensor chip $21_Z$.

The first optical signal output from the optical sensor chip $21_{k-1}$ propagates through the optical fiber 22A and is output to the optical sensor chip $21_k$. The spot-size conversion unit 211A included in the optical sensor chip $21_k$ converts the spot size of the first optical signal based on the waveguide inside the optical sensor chip $21_k$. The processing described so far is the processing of step ST1*b*.

In the optical sensor chip $21_k$, the first optical signal is split to the changer unit 213 and the spot-size conversion unit 216A by the optical path splitter unit 212A (step ST2*b*). When the optical path splitter unit 212A splits the first optical signal to the changer unit 213 (step ST2*b*; B1), the first optical signal is incident on the changer unit 213.

The waveguide 2132, which is a ring resonator, extracts a signal component with the wavelength $\lambda_k$ from the first optical signal incident on the changer unit 213 (step ST3*b*). In a case where the wavelength $\lambda$ of the first optical signal incident on the changer unit 213 is the signal component with the waveguide $\lambda_k$ (step ST3*b*; YES), in the region B illustrated in FIG. 8, the changer unit 213 extracts the signal component with the wavelength $\lambda_k$ from the first optical signal, and the extracted signal component circulates in the waveguide 2132 and resonates (step ST4*b*).

While the signal component circulates in the ring resonator, the intensity of the signal component with the wavelength $\lambda_k$ of the first optical signal decreases in proportion to the moisture content (step ST5*b*). The signal component having circulated in the ring resonator returns to the waveguide 2131 again and is emitted from the changer unit 213. In addition, in the region B, the signal component with the wavelength $\lambda$ other than the wavelength $\lambda_k$ is not extracted from the first optical signal (step ST3*b*; NO) and the signal component with the wavelength $\lambda$ ($\neq\lambda_k$) of the first optical signal directly propagates through the waveguide 2131 and is emitted from the changer unit 213.

In the optical sensor chip $21_k$, the spot-size conversion unit 216B receives the second optical signal from the optical sensor chip $21_{k+1}$. The multiplexer unit 214 multiplexes the second optical signal and the first optical signal emitted from the changer unit 213 (step ST6*b*). The spot-size conversion unit 211B converts the spot size of the optical signal multiplexed by the multiplexer unit 214 based on the optical fiber 22B (step ST7*b*).

In the optical sensor chip $21_k$, the optical signal whose spot size has been converted by the spot-size conversion unit 211B is output to the optical sensor chip $21_{k-1}$ through the optical fiber 22B (step ST8*b*). In this way, the optical signal in which the first optical signal is multiplexed sequentially propagates toward the optical sensor chip $21_1$ in the optical sensor unit 2.

In a case where the optical path splitter unit 212A splits the first optical signal to the spot-size conversion unit 216A (step ST2*b*; B2), the spot-size conversion unit 216A converts the spot size of the first optical signal based on the optical fiber 22A, and outputs the first optical signal to the optical sensor chip $\mathbf{21}_{k+1}$ (step ST9*b*).

Figure 10:
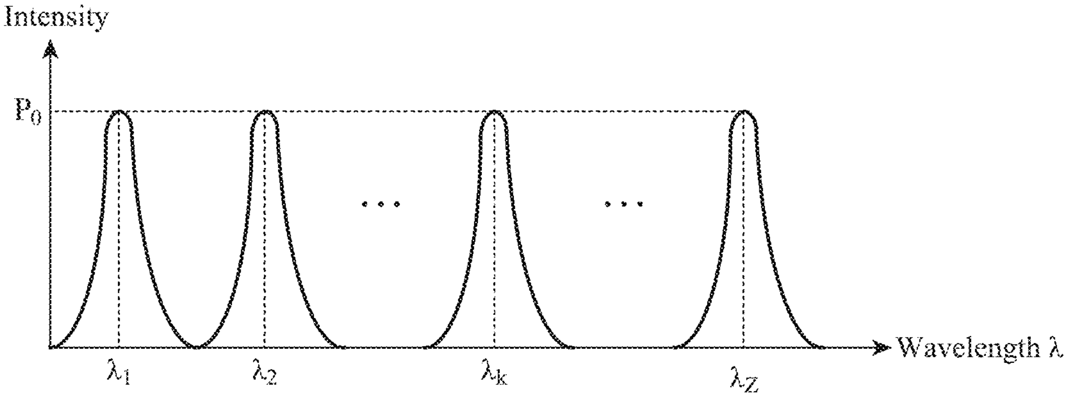
FIG. 10 is a graph illustrating a relationship between the wavelength and the intensity of an optical signal propagating through the optical sensor chip of the optical sensor unit in which the specimen is not disposed.

FIG. 10 is a graph illustrating a relationship between the wavelength and the intensity of a first optical signal propagating through the optical sensor chip $\mathbf{21}_k$ of the optical sensor unit 2 in which the specimen 100 is not disposed. In FIG. 10, the horizontal axis represents the wavelength included in the first optical signal, and the vertical axis represents the intensity of each wavelength of the first optical signal. The specimen 100 is not disposed in the optical sensor unit 2, and there is no absorption of the first optical signal by water present inside or around the specimen 100. Therefore, as illustrated in FIG. 10, the intensities of Z first optical signals with the wavelengths $\lambda_1$ to $\lambda_Z$ in the absorption wavelength band of water are constant at an intensity $P_0$.

Figure 11:
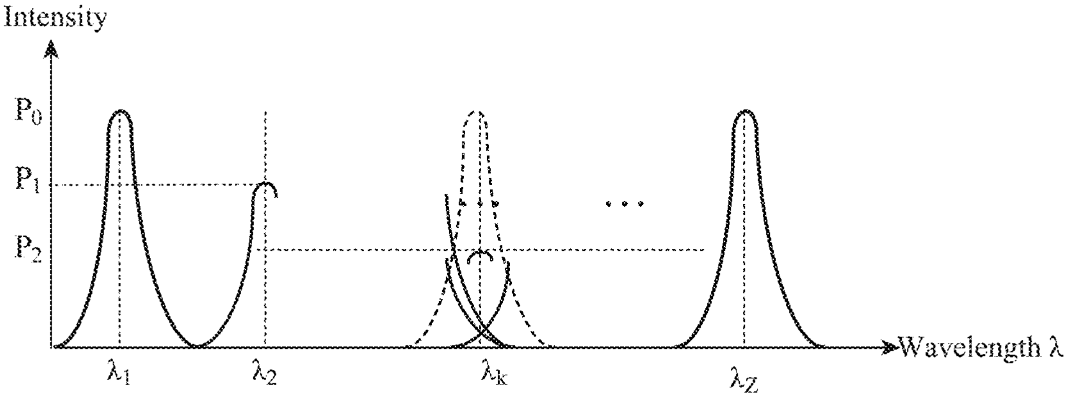
FIG. 11 is a graph illustrating a relationship between the wavelength and the intensity of an optical signal propagating through the optical sensor chip of the optical sensor unit in which the specimen is disposed.

FIG. 11 is a graph illustrating a relationship between the wavelength and the intensity of a first optical signal propagating through the optical sensor chip $\mathbf{21}_k$ of the optical sensor unit 2 in which the specimen 100 is disposed. In FIG. 11, the horizontal axis represents the wavelength included in the first optical signal, and the vertical axis represents the intensity of the first optical signal. In a case where the specimen 100 is disposed in the optical sensor unit 2, moisture present inside the specimen 100 absorbs a signal component with the wavelength 4 in the first optical signal.

For example, the signal component with the wavelength $\lambda_2$ has an intensity $P_1$ lower than the intensity $P_0$ when the specimen 100 is not disposed, and the signal component with the wavelength $\lambda_k$ has an intensity $P_2$ lower than the intensity $P_0$ when the specimen 100 is not disposed. This means that the first optical signal propagates from the optical sensor chip $\mathbf{21}_1$ to the optical sensor chip $\mathbf{21}_Z$, so that the signal component with the wavelength $\lambda_k$ included in the first optical signal is absorbed by the moisture of the specimen 100.

The analysis unit 42 can measure the moisture content inside or around the specimen 100 by analyzing the amount of change ($P_0-P_1$ and $P_0-P_2$) in the intensity of the signal component with the resonance wavelength $\lambda_k$ set in each of the Z optical sensor chips $\mathbf{21}_k$.

Figure 12:
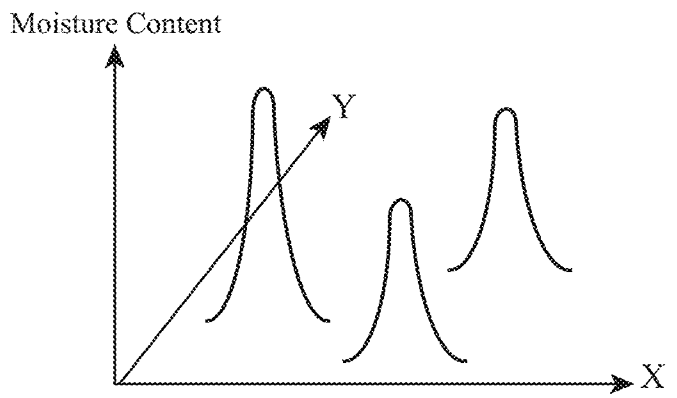
FIG. 12 is a graph illustrating a relationship between the position of the optical sensor chip in the optical sensor unit in which the specimen is disposed and the moisture content of the specimen.

FIG. 12 is a graph illustrating a relationship between the position of the optical sensor chip $\mathbf{21}_k$ in the optical sensor unit 2 in which the specimen 100 is disposed and the moisture content of the specimen 100. The analysis unit 42 specifies the position of the optical sensor chip $\mathbf{21}_k$ in the XY coordinate system set in the optical sensor unit 2 using the propagation time difference calculated from the pulse of a first optical signal transmitted to the optical sensor chip $\mathbf{21}_1$ and the pulse of a second optical signal received from the optical sensor chip $\mathbf{21}_1$.

The analysis unit 42 measures the moisture content of the specimen 100 corresponding to each position of the optical sensor chip $\mathbf{21}_k$, and outputs information indicating the moisture content at each position of the optical sensor chip $\mathbf{21}_k$ to the display unit 5 as measurement results. For example, as illustrated in FIG. 12, the display unit 5 displays a three-dimensional graph illustrating the moisture content of the specimen 100 at each position of the optical sensor chip $\mathbf{21}_k$ in the XY coordinate system.

FIG. 12 illustrates the case of detecting the moisture content of the specimen 100 at each position of the optical sensor chip $\mathbf{21}_k$, but Z optical sensor chips $\mathbf{21}_k$ may change the characteristics of the input optical signal depending on a plurality of types of states of the specimen 100. For example, the optical sensor unit 2 includes an optical sensor chip that changes the characteristics of the first optical signal depending on the temperature of the specimen 100, an optical sensor chip that changes the characteristics of the first optical signal depending on the moisture content of the specimen 100, and an optical sensor chip that changes the characteristics of the first optical signal depending on the pressure from the specimen 100.

Apart of the Z optical sensor chips $\mathbf{21}_k$ may be optical sensor chips that change the characteristics of the optical signal depending on the moisture content of the specimen 100, and the remaining may be optical sensor chips that change the characteristics of the optical signal depending on the temperature of the specimen 100.

The changer unit 213 may include a ring resonator that changes the characteristics of the first optical signal depending on the moisture content of the specimen 100 and a ring resonator that changes the characteristics of the first optical signal depending on the temperature of the specimen 100. As a result, one optical sensor chip may change the characteristics of the first optical signal depending on a plurality of types of states of the specimen 100.

The optical sensor unit 2 may be formed by continuously connecting a plurality of optical sensor chips that change the characteristics of the first optical signal depending on each of a plurality of types of states of the specimen 100. For example, in the above unit, an optical sensor chip that detects the temperature of the specimen 100, an optical sensor chip that detects the moisture content of the specimen 100, and an optical sensor chip that detects the pressure from the specimen 100 are optically connected via the optical fiber 22.

In a case where the optical sensor chip $\mathbf{21}_k$ is used to detect the temperature of the specimen 100, as illustrated in FIG. 8, the waveguide 2132 in which the effective curvature radius R changes with a temperature change $\Delta T$ is used in the changer unit 213. For example, the waveguide 2132 satisfies $2\pi\times\Delta R\times n_{eff}=m\times\Delta\lambda$, which is a relational expression indicating the correspondence relationship between the amount of change $\Delta R$ in curvature radius and the amount of shift $\Delta X$ in resonance wavelength. The analysis unit 42 calculates the amount of change $\Delta R$ in the curvature radius of the waveguide 2132 on the basis of the amount of shift $\Delta\lambda$ of the resonance wavelength between the first optical signal and the second optical signal, and calculates the temperature change $\Delta T$ using $\Delta R$. As a result, the optical sensor chip $\mathbf{21}_k$ can detect the temperature of the specimen 100.

Figure 13:
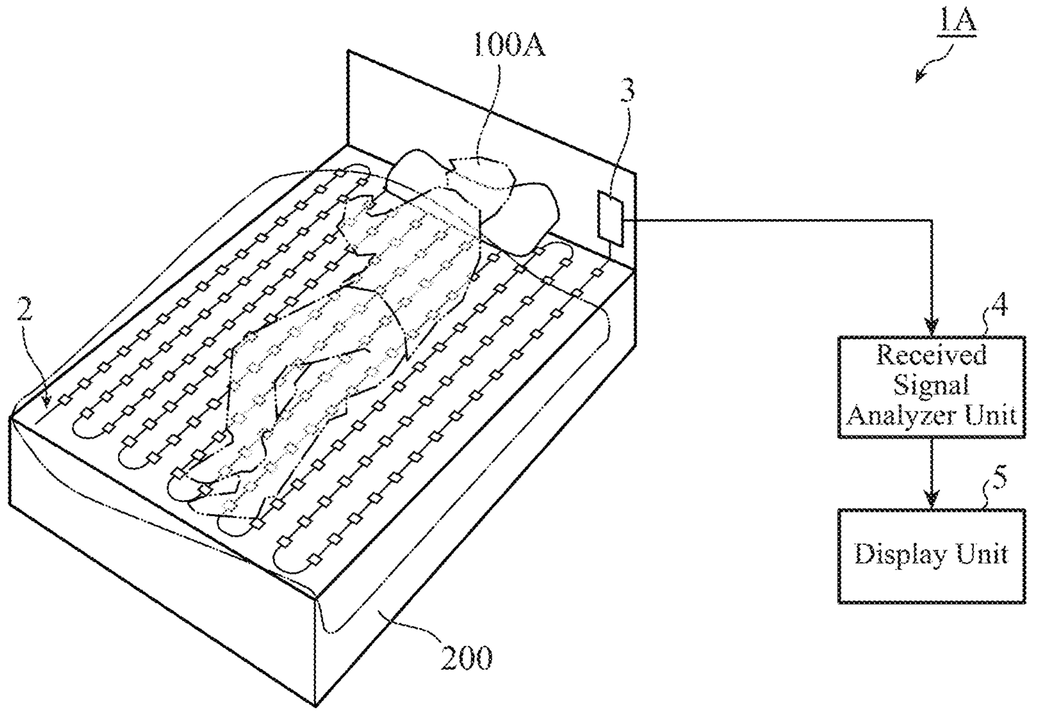
FIG. 13 is a configuration diagram illustrating a first modification of the optical sensor system according to the first embodiment.

FIG. 13 is a configuration diagram illustrating an optical sensor system 1A that is a first modification of the optical sensor system 1. As illustrated in FIG. 13, the optical sensor unit 2 is laid on a bed 200, and the specimen is a person 100A lying on the bed 200. By the person 100A lying on the bed 200, the person 100A is disposed on the optical sensor unit 2. The optical sensor system 1A measures the state of the person 100A lying on the bed 200.

The analysis unit 42 can measure the temperature, the amount of perspiration, or the sleeping position of the person 100A on the basis of the change in the characteristics of the first optical signal for each optical sensor chip $\mathbf{21}_k$ in the optical sensor unit 2. For example, the analysis unit 42 measures the amount of perspiration of the person 100A and the temporal change thereof at each position of the optical sensor chip $\mathbf{21}_k$, and outputs the measurement results to the display unit 5. As a result, the display unit 5 can graphically display the temporal change in the distribution of the amount of perspiration of the person 100A.

Figure 14:
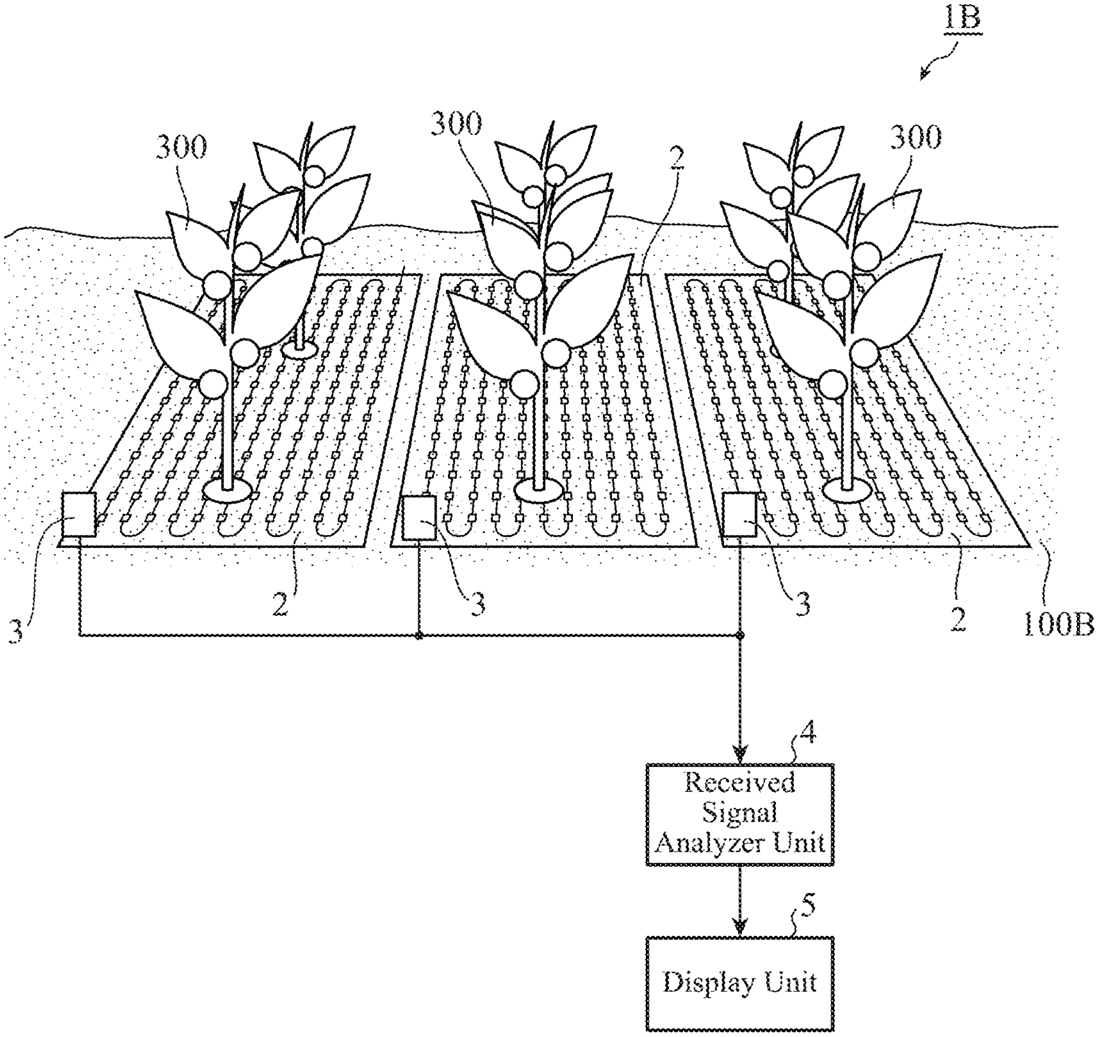
FIG. 14 is a configuration diagram illustrating a second modification of the optical sensor system according to the first embodiment.

FIG. 14 is a configuration diagram illustrating an optical sensor system 1B that is a second modification of the optical sensor system. As illustrated in FIG. 14, the optical sensor unit 2 is buried in a farmland, and the specimen 100 is farmland soil 100B. The optical sensor system 1B measures the state of the farmland soil 100B. For example, the analysis unit 42 measures the temperature, the moisture content, or the nutrient component of the soil 100B on the basis of the change in the characteristics of a first optical signal for each optical sensor chip $21_k$ in the optical sensor unit 2.

For example, in the case of detecting the carbon dioxide concentration or the calcium concentration of the soil 100B, the wavelength $\lambda_k$ in the absorption wavelength band of carbon dioxide or calcium is set in the changer unit 213 included in each of Z optical sensor chips $21_k$. Similarly to the measurement of the moisture content of the specimen 100, the intensity of the first optical signal circulated in a ring resonator and resonated decreases depending on the carbon dioxide concentration or the calcium concentration of the soil 100B.

The analysis unit 42 measures the temperature, the moisture content, or the nutrient component of the soil 100B and the temporal change thereof at each position of the optical sensor chip $21_k$ on the basis of the change in the intensity of the first optical signal, and outputs the measurement results to the display unit 5. The display unit 5 graphically displays, for example, the temporal change in the distribution of the temperature, the moisture content, or the nutrient component of the soil 100B.

Figure 15:
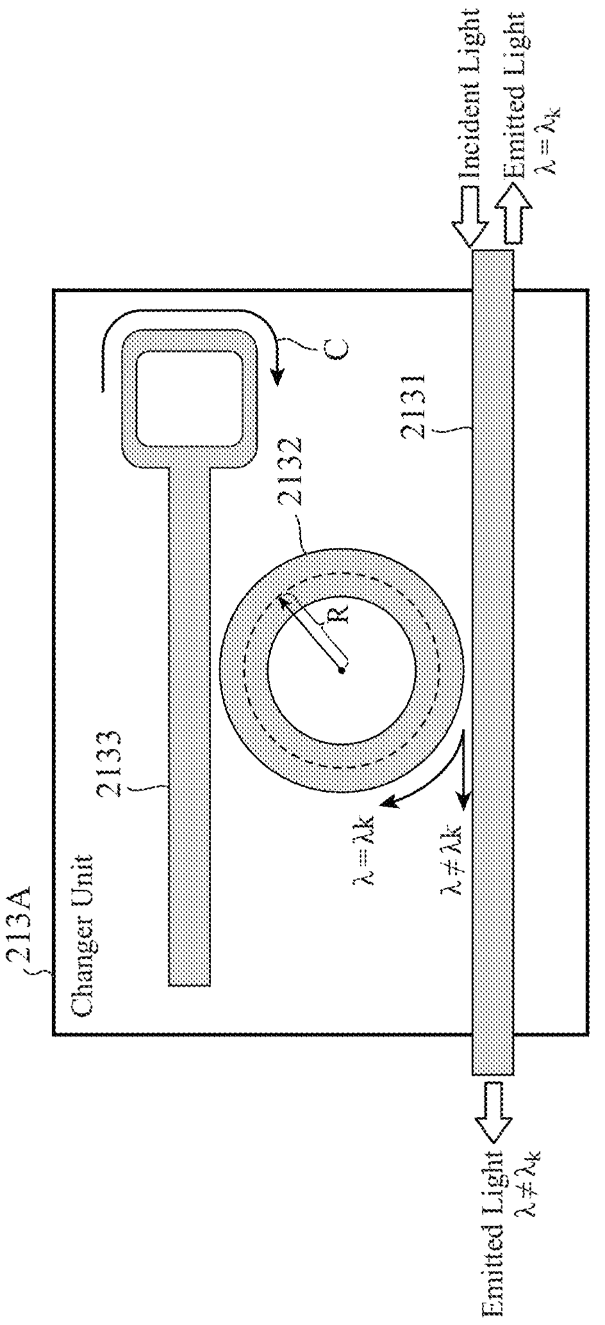
FIG. 15 is a configuration diagram illustrating a first modification of the changer unit.

FIG. 15 is a configuration diagram illustrating a changer unit 213A that is a first modification of the changer unit 213. In FIG. 15, the changer unit 213A is obtained by adding a waveguide 2133 to the changer unit 213. The waveguide 2133 includes a band-like line path provided close to the waveguide 2132 which is a ring resonator and a ring-like line path provided at an end portion thereof.

The optical signal component with the resonance wavelength $\lambda_k$ propagates from the waveguide 2131 to the waveguide 2132 and resonates, then propagates through the waveguide 2133, and the optical path is folded in a direction indicated by an arrow C. As illustrated in FIG. 15, the folded optical signal component propagates through the waveguide 2132 again and resonates, and then propagates through the waveguide 2131 and is emitted as the emitted light with the wavelength $\lambda_k$.

Figure 16:
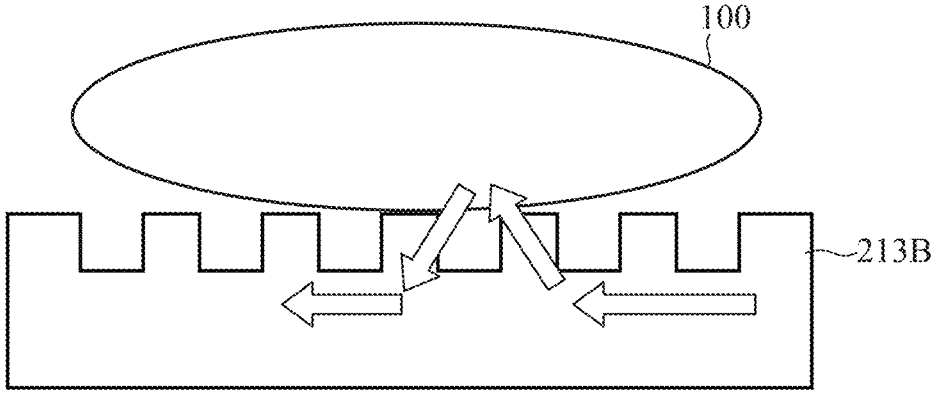
FIG. 16 is a configuration diagram illustrating a second modification of the changer unit.

FIG. 16 is a configuration diagram illustrating a changer unit 213B that is a second modification of the changer unit 213. In FIG. 16, the changer unit 213B is an optical element that outputs a part of the first optical signal to the outside, and receives reflected light obtained by reflecting the output light. For example, the changer unit 213B is a grating coupler. The characteristics of the first optical signal emitted from the changer unit 213B are changed depending on the state of the specimen 100 outside, and the first optical signal is reflected by the specimen 100, and input to the changer unit 213B again. The first optical signal whose characteristics have been changed depending on the state of the specimen 100 is output to the spot-size conversion unit 216A.

Next, a hardware configuration that implements the functions of the optical transceiver unit 3 and the received signal analyzer unit 4 will be described. The functions of the optical transmitter unit 31, the optical receiver unit 32, the identification unit 41, and the analysis unit 42 illustrated in FIGS. 1 and 3 are implemented by a processing circuit. That is, the optical transmitter unit 31, the optical receiver unit 32, the identification unit 41, and the analysis unit 42 include a processing circuit for performing the processing from step ST1 to step ST4 illustrated in FIG. 6. The processing circuit may be dedicated hardware, or may be a central processing unit (CPU) that executes a program stored in a memory.

Figure 17A:
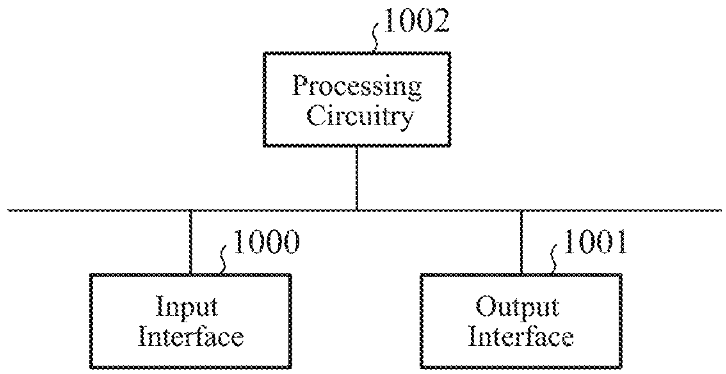
FIGS. 17A and 17B are block diagrams illustrating a hardware configuration that implements functions of an optical transceiver unit and a received signal analyzer unit.
Figure 17B:
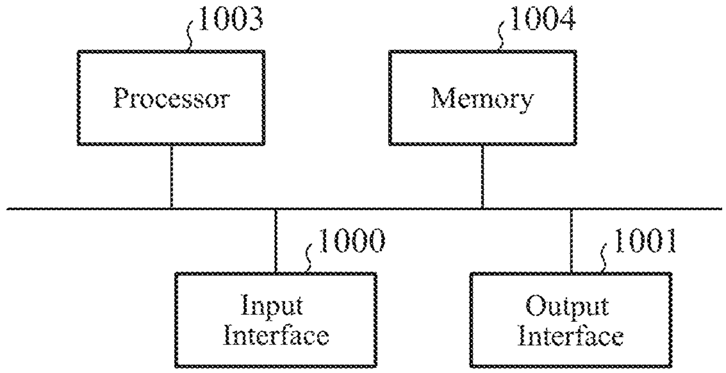

FIG. 17A is a block diagram illustrating a hardware configuration that implements the functions of the optical transceiver unit 3 and the received signal analyzer unit 4. In addition, FIG. 17B is a block diagram illustrating a hardware configuration that executes software that implements the functions of the optical transceiver unit 3 and the received signal analyzer unit 4. In FIGS. 17A and 17B, an input interface 1000 is an interface that relays an electrical signal corresponding to a second optical signal received by a light receiving element. An output interface 1001 is an interface that relays measurement result information output to the display unit 5.

In a case where the processing circuit is a processing circuit 1002 of dedicated hardware illustrated in FIG. 17A, the processing circuit 1002 corresponds to, for example, a single circuit, a composite circuit, a programmed processor, a parallel programmed processor, an application specific integrated circuit (ASIC), a field-programmable gate array (FPGA), or a combination thereof. The functions of the optical transmitter unit 31, the optical receiver unit 32, the identification unit 41, and the analysis unit 42 may be implemented by separate processing circuits, or these functions may be collectively implemented by one processing circuit.

In a case where the processing circuit is a processor 1003 illustrated in FIG. 17B, the functions of the optical transmitter unit 31, the optical receiver unit 32, the identification unit 41, and the analysis unit 42 are implemented by software, firmware, or a combination of software and firmware. Note that software or firmware is described as a program and stored in a memory 1004.

The processor 1003 reads and executes the program stored in the memory 1004, thereby implementing the functions of the optical transmitter unit 31, the optical receiver unit 32, the identification unit 41, and the analysis unit 42. For example, the optical sensor system 1 includes the memory 1004 for storing a program that allows the processing from step ST1 to step ST4 in the flowchart illustrated in FIG. 6 to be performed when executed by the processor 1003. These programs cause a computer to execute procedures or methods of processing performed by the optical transmitter unit 31, the optical receiver unit 32, the identification unit 41, and the analysis unit 42. The memory 1004 may be a computer-readable storage medium that stores a program for causing a computer to function as the optical transmitter unit 31, the optical receiver unit 32, the identification unit 41, and the analysis unit 42.

The memory 1004 corresponds, for example, to a nonvolatile or volatile semiconductor memory such as a random access memory (RAM), a read only memory (ROM), a flash memory, an erasable programmable read only memory (EPROM), or an electrically-EPROM (EEPROM), a magnetic disk, a flexible disk, an optical disk, a compact disk, a mini disk, a DVD, or the like.

In addition, some of the functions of the optical transmitter unit 31, the optical receiver unit 32, the identification unit 41, and the analysis unit 42 may be implemented by dedicated hardware, and some of the functions may be implemented by software or firmware. For example, the functions of the optical transmitter unit 31 and the optical receiver unit 32 are implemented by the processing circuit 1002 that is dedicated hardware, and the functions of the identification unit 41 and the analysis unit 42 are implemented by the processor 1003 reading and executing the program stored in the memory 1004. As described above, the processing circuit can implement the functions by hardware, software, firmware, or a combination thereof.

Figure 18:
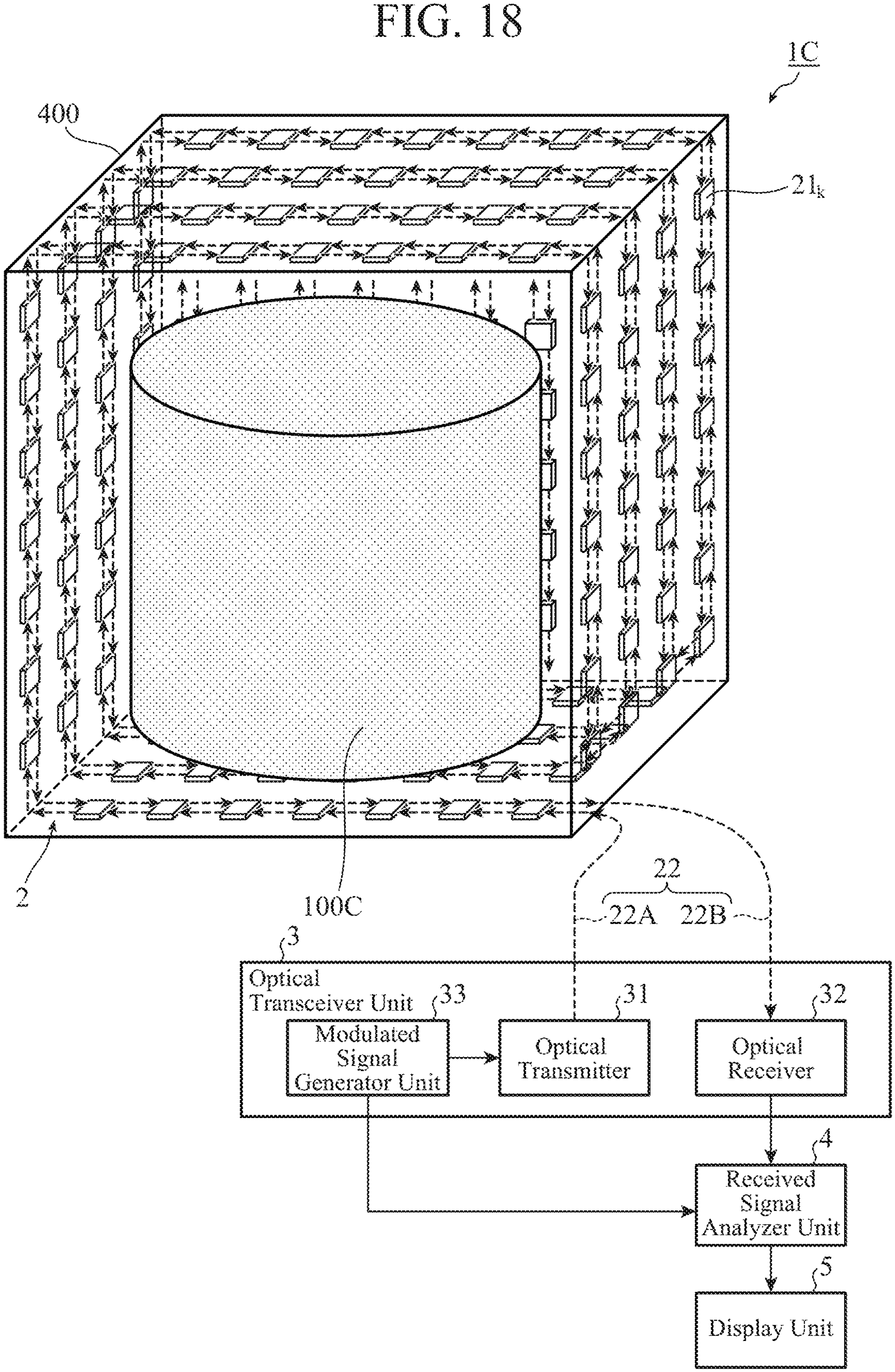
FIG. 18 is a configuration diagram illustrating a third modification of the optical sensor system according to the first embodiment.

FIG. 18 is a configuration diagram illustrating an optical sensor system 1C that is a third modification of the optical sensor system 1. In the optical sensor system 1C, the optical sensor unit 2 is three-dimensionally disposed in a closed space. For example, as illustrated in FIG. 18, by providing the optical sensor unit 2 in such a manner as to cover a columnar specimen 100C, the optical sensor system 1C can determine the entire specimen 100C as a measurement portion, and the measurement range is extended.

In FIG. 18, the optical sensor unit 2 is attached to all the inner wall surfaces of a box 400 in such a manner as to cover the columnar specimen 100C. By disposing the specimen 100C inside the box 400, the optical sensor unit 2 can detect the state of all the portions of the specimen 100C. For example, in a case where the optical sensor unit 2 is two-dimensionally disposed, the state of a portion of the specimen 100C that is not close to the optical sensor chip $21_k$ is not detected, but by three-dimensionally disposing the optical sensor unit 2 in the closed space, the optical sensor system 1C can measure the state of all the portions of the specimen 100C.

Note that the box 400 does not need to be a closed space. For example, the optical sensor unit 2 may be three-dimensionally disposed in a space where a part is opened, such as a pipe or a tunnel. In this case, the optical sensor unit 2 cannot be disposed in the opened portion, but the optical sensor unit 2 can be disposed around the specimen 100C except for this portion. Therefore, the optical sensor system 1C can determine all the portions of the specimen 100C facing the optical sensor unit 2 as measurement portions.

In addition, it is assumed that the closed space is a cardboard box including the optical sensor unit 2 on the inner wall surface, a food is disposed as the specimen 100C inside the cardboard box, and the optical sensor chip $21_k$ in the optical sensor unit 2 is, for example, an optical sensor chip that detects the moisture content of the food or the humidity inside the cardboard box. In this case, the optical sensor system 1C can measure the moisture distribution of the food or the humidity distribution of the food inside the cardboard box using the optical sensor unit 2. A food manager can recognize the temporal change in the moisture distribution of the food or the humidity distribution of the food on the basis of the measurement results of the moisture distribution of the food or the humidity distribution of the food. The measurement results can also be used to predict the occurrence of rotting of the food.

The closed space may be a bathroom including the optical sensor unit 2 on the wall surface, and the atmosphere inside the bathroom may be the specimen 100C. That is, the optical sensor chip $21_k$ detects the humidity of the atmosphere inside the bathroom. The optical sensor system 1C can measure the humidity distribution of the atmosphere inside the bathroom using the optical sensor unit 2. As a result, a user can recognize the temporal change in the humidity distribution of the atmosphere inside the bathroom. In addition, the measurement results can be used to predict the occurrence of mold on the bathroom wall surface. As described above, the optical sensor system 1C can determine the entire specimen 100C as a measurement portion, and the measurement range is extended.

As described above, according to the optical sensor chip $21_k$ of the first embodiment, the specimen 100 is disposed in the optical sensor unit in which Z optical sensor chips $21_Z$ are connected, and the optical signal propagated through the optical sensor unit is changed in each optical sensor chip $21_k$ depending on the state of the specimen 100. As a result, since the state of the specimen 100 detected by each optical sensor chip $21_k$ can be specified by analyzing the change in the optical signal depending on the state of the specimen 100, the optical sensor chip $21_k$ can be used to collectively measure the state of a plurality of portions of the specimen 100.

In the optical sensor chip $21_k$ according to the first embodiment, the spot-size conversion unit 211A and the spot-size conversion unit 211B constitute one interface unit. The spot-size conversion unit 216A and the spot-size conversion unit 216B constitute one interface unit. As a result, the number of components for installing the optical sensor chip $21_k$ is reduced, and the installation work is also simplified.

The optical sensor chip $21_k$ according to the first embodiment includes the optical path length adder unit 215A that is an optical path for delaying the first optical signal output by the spot-size conversion unit 216A, and the optical path splitter unit 212A that splits the first optical signal input by the spot-size conversion unit 211A or the first optical signal changed by the changer unit 213 depending on the state of the specimen 100. As a result, by analyzing the propagation time of the first optical signal, it is possible to identify the optical sensor chip $21_k$.

In the optical sensor chip $21_k$ according to the first embodiment, the first optical signal is an optical signal with one predetermined wavelength, and an electrical signal obtained by modulating one of an intensity characteristic, a phase characteristic, and a frequency characteristic is applied. As described above, the optical sensor chip $21_k$ can use various modulated signals as measurement light.

In the optical sensor chip $21_k$ according to the first embodiment, the first optical signal is an optical signal with a plurality of wavelengths. The optical path splitter unit 212A selects a first optical signal with a predetermined wavelength from the first optical signal input by the spot-size conversion unit 211A, and outputs the selected first optical signal to the changer unit 213. As a result, the first optical signal with the predetermined wavelength can be propagated to the changer unit 213.

The optical sensor system 1 according to the first embodiment includes the optical sensor unit 2, the optical transmitter unit 31 that transmits the first optical signal to the spot-size conversion unit 211A of the optical sensor chip $21_1$ in the optical sensor unit 2, the optical receiver unit 32 that receives the optical signal in which the first optical signal changed depending on the state of the specimen 100 is multiplexed from the spot-size conversion unit 211B of the optical sensor chip $21_1$, the identification unit 41 that identifies each optical sensor chip using a received signal of the optical receiver unit 32, and the analysis unit 42 that specifies the state of the specimen 100 for each optical sensor chip $21_k$ by analyzing the received signal of the optical receiver unit 32. With these configurations, the optical sensor system 1 can collectively measure the state of a plurality of portions of the specimen 100.

In the optical sensor system 1 according to the first embodiment, the analysis unit 42 specifies the change in the first optical signal depending on the state of the specimen 100 by analyzing any one of the intensity characteristic, the phase characteristic, the frequency characteristic, and the wavelength characteristic of the received signal of the second optical signal. As a result, the optical sensor system 1 can collectively measure the state of a plurality of portions of the specimen 100.

In the optical sensor system 1 according to the first embodiment, the Z optical sensor chips $\mathbf{21}_Z$ are continuously connected, and the identification unit 41 associates the first optical signal changed depending on the state of the specimen 100 with the optical sensor chip $\mathbf{21}_k$ by analyzing the delay time of the first optical signal included in the received signal of the optical receiver unit 32. By analyzing the delay time of the first optical signal of the pulse, for example, the optical sensor system 1 can identify individual optical sensor chips $\mathbf{21}_k$.

In the optical sensor system 1 according to the first embodiment, the identification unit 41 associates the first optical signal changed depending on the state of the specimen 100 with the optical sensor chip $\mathbf{21}_k$ by analyzing the wavelength of the first optical signal included in the received signal of the optical receiver unit 32. For example, by analyzing the wavelength of the first optical signal that is continuous light in which a plurality of wavelengths are multiplexed, the optical sensor system 1 can identify the individual optical sensor chips $\mathbf{21}_k$.

The measurement method according to the first embodiment is a measurement method of the optical sensor system 1, and includes causing the optical transmitter unit 31 to transmit the first optical signal to the spot-size conversion unit 211A of the optical sensor chip $\mathbf{21}_1$ at an end portion of the optical sensor unit 2, causing the optical receiver unit 32 to receive the optical signal in which the first optical signal changed depending on the state of the specimen 100 is multiplexed from the spot-size conversion unit 211B of the optical sensor chip $\mathbf{21}_1$ at the end portion of the optical sensor unit 2, causing the identification unit 41 to identify each optical sensor chip $\mathbf{21}_k$ using a received signal of the optical receiver unit 32, and causing the analysis unit 42 to specify the state of the specimen 100 for each optical sensor chip $\mathbf{21}_k$ by analyzing the received signal of the optical receiver unit 32. With this method, the state of a plurality of portions of the specimen 100 can be collectively measured.

Second Embodiment

Figure 19:
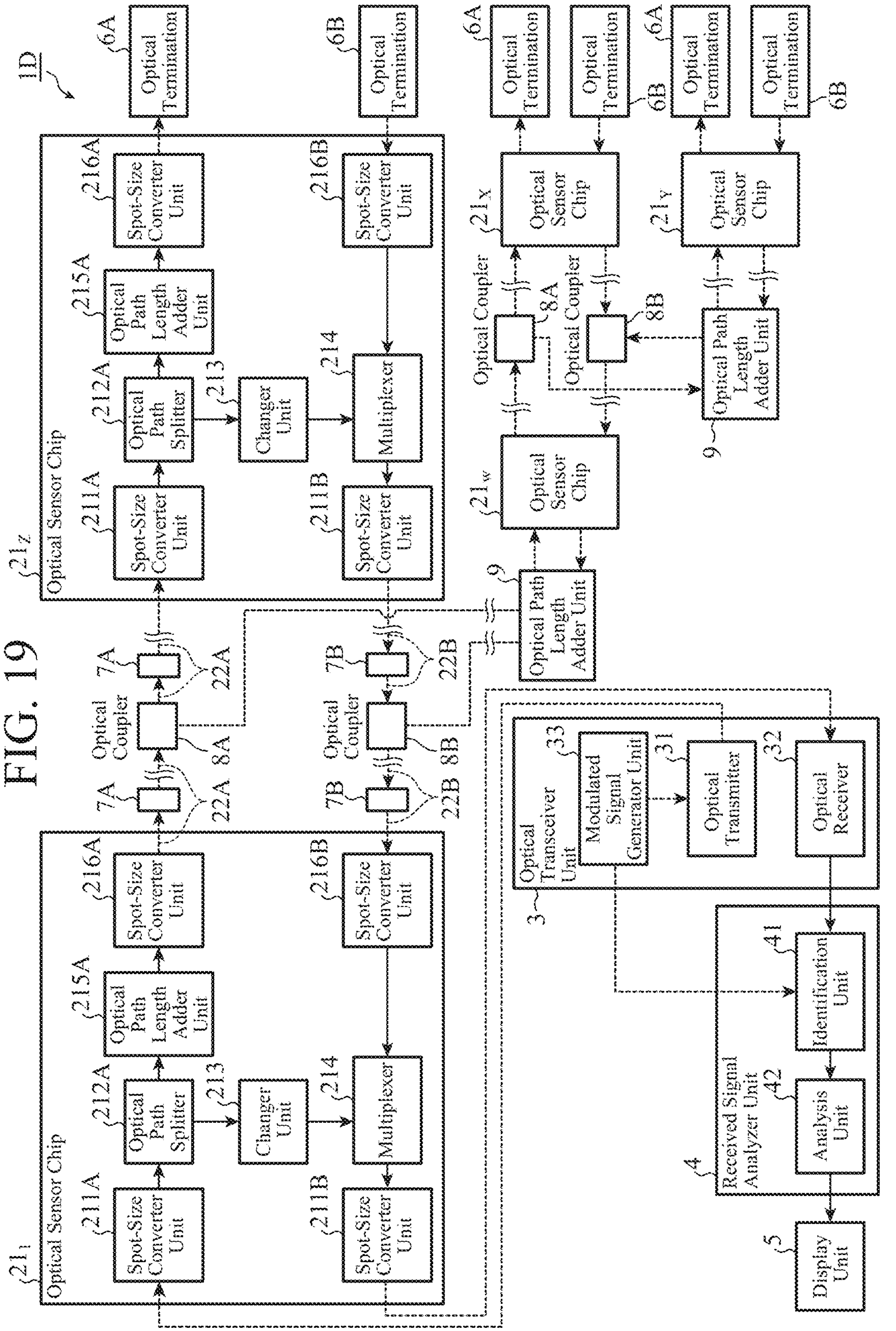
FIG. 19 is a configuration diagram illustrating an optical sensor system according to a second embodiment.

FIG. 19 is a configuration diagram illustrating an optical sensor system 1D according to a second embodiment. In FIG. 19, the optical sensor unit 2 of the optical sensor system 1D includes a portion in which Z optical sensor chips $\mathbf{21}_k$ are continuously connected, and a sensor array split from this portion via an optical coupler 8A, an optical coupler 8B, and an optical path length adder unit 9. In the sensor array, a plurality of optical sensor chips $\mathbf{21}_k$, for example, an optical sensor chip $\mathbf{21}_W$, an optical sensor chip $\mathbf{21}_X$, and an optical sensor chip $\mathbf{21}_Y$ are continuously connected, and another sensor array may be split from this sensor array via the optical coupler 8B and the optical path length adder unit 9.

The optical coupler 8A is provided in the optical fiber 22A connected between the optical sensor chip $\mathbf{21}_k$ and the optical sensor chip $\mathbf{21}_{k+1}$, and is connected to the optical sensor chips and the sensor array. The optical coupler 8A splits the first optical signal propagated from the optical sensor chip $\mathbf{21}_k$ to the optical sensor chip $\mathbf{21}_{k-1}$ to the sensor array via the optical fiber 22A.

In addition, the optical coupler 8B is provided in the optical fiber 22B connected between the optical sensor chip $\mathbf{21}_k$ and the optical sensor chip $\mathbf{21}_{k+1}$, and is connected to the optical sensor chips and the sensor array. Similarly to the optical coupler 8A, the optical coupler 8B splits the second optical signal propagated through the sensor array to the sensor array in which the optical sensor chip $\mathbf{21}_1$ is connected via the optical fiber 22B.

The optical path length adder unit 9 is a second optical path length adder unit that is an optical path with a predetermined optical path length for delaying the first optical signal propagating through the sensor array. For example, the optical path length adder unit 9 is obtained by processing the optical fiber 22 in such a manner as to delay the propagation of a signal or is an optical waveguide that delays the propagation of a signal. In order to add the propagation time unique to the sensor array to the first optical signal propagating through the sensor array, the optical path length adder unit 9 is disposed at the subsequent stage of the optical couplers 8A and 8B. Note that, as long as the optical path length adder unit 9 can add a predetermined propagation time to the optical signal propagating through the sensor array, the arrangement place thereof is irrelevant.

In the portion from the optical sensor chip $\mathbf{21}_1$ to the optical sensor chip $\mathbf{21}_Z$ in the optical sensor system 1D, the optical path length adder unit 215A may add the optical path length for each optical sensor chip $\mathbf{21}_k$, and in the sensor array split from the optical sensor unit from the optical sensor chip $\mathbf{21}_1$ to the optical sensor chip $\mathbf{21}_Z$, the optical path length adder unit 9 may add the optical path length for each sensor array as processing of identifying the sensor array. In this case, the optical sensor chip $\mathbf{21}_k$ constituting the sensor array does not need to include the optical path length adder unit 215A.

In the optical transceiver unit 3, the optical transmitter unit 31 transmits the first optical signal to the optical sensor chip $\mathbf{21}_1$ through the optical fiber 22A. The modulated signal generator unit 33 generates an electrical modulation signal with a predetermined modulation scheme for modulating light emitted from a light emitting element, and outputs the electrical modulation signal to the optical transmitter unit 31 and an identification unit 41. The optical transmitter unit 31 outputs a first optical signal obtained by modulating the light emitted from the light emitting element on the basis of the electrical modulation signal to the optical fiber 22A connected to the optical sensor chip $\mathbf{21}_1$.

The optical receiver unit 32 receives an optical signal from the optical sensor chip $\mathbf{21}_1$ through the optical fiber 22B. The optical receiver unit 32 includes a light receiving element, and the light receiving element converts the optical signal into an electrical signal. The light emitting element and the light receiving element may be provided separately, or may be an optical sensor in which the light emitting element and the light receiving element are integrated into one. The optical transceiver unit 3 may be provided separately from the optical sensor unit 2, or may be provided in the optical sensor unit 2. For example, the optical transceiver unit 3 may be integrated on an InP substrate provided in a part of the optical sensor unit 2.

In the optical sensor chips $\mathbf{21}_X$, $\mathbf{21}_Y$, and $\mathbf{21}_Z$, the optical termination 6A is a portion provided at the end portion of the optical fiber 22A in such a manner as to minimize light reflection. The first optical signal sequentially propagated from the optical sensor chip $\mathbf{21}_1$ to the optical sensor chips $\mathbf{21}_X$, $\mathbf{21}_Y$, and $\mathbf{21}_Z$ is terminated at the optical termination 6A. In the optical sensor chip $\mathbf{21}_X$, $\mathbf{21}_Y$, and $\mathbf{21}_Z$, the optical termination 6B is a portion provided at the end portion of the optical fiber 22B in such a manner as to minimize light reflection. The second optical signal is terminated at the optical termination 6B. The optical terminations 6A and 6B may be one optical termination for both transmission and reception.

In the received signal analyzer unit 4, the identification unit 41 identifies each optical sensor chip $21_k$ using the received signal of the optical signal received by the optical receiver unit 32. For example, the identification unit 41 detects the received signal on the basis of the electrical modulation signal generated by the modulated signal generator unit 33 and reads the wavelength value thereof, thereby specifying the identification number k of the modulated optical sensor chip $21_k$. As a result, the identification unit 41 identifies each of the optical sensor chips $21_k$.

The identification unit 41 may identify the optical sensor chip $21_k$ by comparing the propagation of the pulse of the first optical signal (the first optical signal before transmission) with the propagation of the pulse of the received signal of the optical receiver unit 32. In this case, the identification unit 41 identifies the optical sensor chip $21_k$ corresponding to the received signal by specifying the identification number k corresponding to the propagation time of the received signal of the optical receiver unit 32. The identification unit 41 can also specify the position of the optical sensor chip $21_k$ corresponding to the identification number k.

Furthermore, the identification unit 41 calculates the propagation time of the received signal of the optical receiver unit 32 by comparing the propagation of the pulse of the first optical signal (the first optical signal before transmission) with the propagation of the pulse of the received signal of the optical receiver unit 32. In the identification unit 41, the propagation time corresponding to the optical path length added in each sensor array and the identification number of the sensor array are registered in association with each other. The identification unit 41 can identify the sensor array corresponding to the received signal of the optical receiver unit 32 by specifying the identification number corresponding to the propagation time. In addition, the identification unit 41 can also specify the position of the sensor array corresponding to the identification number.

Figure 20:
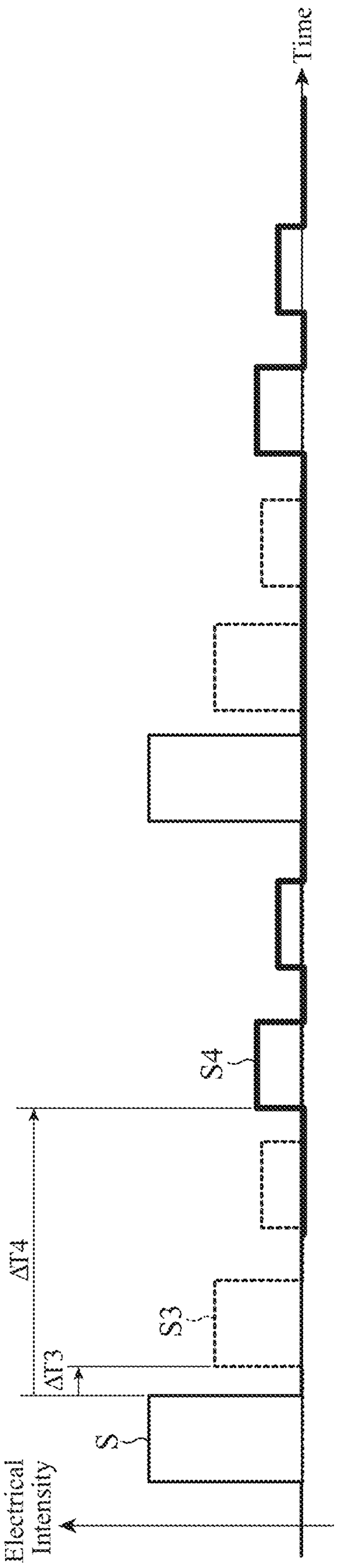
FIG. 20 is a waveform diagram illustrating time waveforms of a first optical signal before transmission and a received signal of a second optical signal in the optical sensor system according to the second embodiment.

FIG. 20 is a waveform diagram illustrating time waveforms of a first optical signal before transmission and a received signal of the optical receiver unit 32 in the optical sensor system 1D, and illustrates a delay of the first optical signal in the sensor array. The modulated signal generator unit 33 generates a pulse modulated signal and applies the pulse modulated signal to the optical transmitter unit 31, so that the first optical signal S illustrated in FIG. 20 is generated. The first optical signal S propagates through the sensor array in the optical sensor unit 2, so that the characteristics of the first optical signal S are changed depending on the state of the specimen 100.

The optical path splitter unit 212A in the optical sensor chips $21_X$, $21_Y$, and $21_Z$, splits the first optical signal input by the spot-size conversion unit 211A to the changer unit 213 and the optical path length adder unit 215A. The first optical signal propagated through the optical path length adder unit 215A and the spot-size conversion unit 216A is terminated by the optical termination 6A connected to each of the optical sensor chips $21_X$, $21_Y$, and $21_Z$.

On the other hand, the changer unit 213 changes the first optical signal depending on the state of the specimen 100. The multiplexer unit 214 multiplexes the first optical signal changed depending on the state of the specimen 100 and the second optical signal input by the spot-size conversion unit 216B, and outputs the multiplexed signal to the spot-size conversion unit 211B. The spot-size conversion unit 211B outputs the first optical signal whose spot size has been converted based on the optical fiber 22B to the optical sensor chips $21_{X-1}$, $21_{Y-1}$, and $21_{Z-1}$ as the second optical signal.

The optical path length adder unit 9 is a second optical path length adder unit that is an optical path with a predetermined optical path length for delaying the first optical signal propagating through the sensor array. As a result, the first optical signal is delayed by the transmission time corresponding to the optical path length added by the optical path length adder unit 9 in each sensor array. A time difference due to the delay in the sensor array occurs in the optical signal received from the optical sensor chip $21_1$ by the optical receiver unit 32.

For example, as illustrated in FIG. 20, a time difference ΔT3 from the first optical signal S occurs in a received signal S3 of the optical receiver unit 32, and a time difference ΔT4 from the first optical signal S occurs in a received signal S4 of the optical receiver unit 32. By analyzing the time differences ΔT3 and ΔT4 in the received signals S3 and S4 of the optical receiver unit 32, the identification unit 41 can identify the optical sensor array that has output the received signal S3 of the optical receiver unit 32 and the optical sensor array that has output the received signal S4 of the optical receiver unit 32. In addition, the identification unit 41 associates an identification number predetermined in the sensor array with each of the received signals S3 and S4 of the optical receiver unit 32.

The first optical signal may be phase-modulated or frequency-modulated. For example, the modulated signal generator unit 33 generates a frequency modulated signal and applies the frequency modulated signal to the optical transmitter unit 31, so that a frequency-modulated first optical signal is generated. By transmitting the first optical signal to the optical sensor chip $21_1$, the optical receiver unit 32 receives the frequency-modulated optical signal. The optical receiver unit 32 performs heterodyne detection on the received signal and the analysis unit 42 specifies the amount of frequency shift of each received signal based on the state of the specimen 100.

The analysis unit 42 specifies the state of the specimen 100 disposed in the optical sensor unit 2 for each optical sensor chip $21_k$ or each sensor array by analyzing the received signal of the optical receiver unit 32. For example, the analysis unit 42 reads the intensity difference of the received signal for each optical sensor chip $21_k$ identified using the identification number k of the optical sensor chip $21_k$, thereby specifying the state of the specimen 100 around the optical sensor chips $21_k$. In addition, the analysis unit 42 reads the intensity difference of the received signal for each sensor array identified using the identification number of the sensor array, thereby specifying the state of the specimen 100 around the sensor arrays.

For example, the first optical signal S multiplexed with the received signals S3 and S4 of the optical receiver unit 32 changes depending on the state of the specimen 100. In the example illustrated in FIG. 20, since the intensity of the first optical signal decreases depending on the state of the specimen 100, an intensity difference from the first optical signal S occurs in the received signal S3, and a larger intensity difference than that of the received signal S3 occurs in the received signal S4. When the identification unit 41 identifies the sensor array, the analysis unit 42 specifies the state of the specimen 100 in each sensor array by analyzing the intensity difference between the received signals S3 and S4 of the optical receiver unit 32 and the first optical signal S. The method of analyzing a received signal is not limited to the intensity analysis of the received signal, and may be analysis of a phase characteristic or a frequency characteristic.

The display unit 5 receives measurement results of the state of the specimen 100 from the received signal analyzer unit 4, and displays the received measurement results. For example, the display unit 5 graphically displays the state of the specimen 100 at the place where the optical sensor chip $\mathbf{21}_k$ is disposed and the state of the specimen 100 in the region where the sensor array is disposed.

In addition, in the optical sensor system 1D, even if each optical sensor array does not have the optical path length adder unit 9, a delay based on the optical path of the sensor array occurs. By analyzing these delay times, it is possible to specify the optical signal propagated through each sensor array. For example, in the first optical signal propagated through the optical sensor chips $\mathbf{21}_k$ included in the optical sensor system 1D, a delay based on the optical path inside each of the optical sensor chips $\mathbf{21}_k$ occurs, and a delay based on the sensor array in which these optical sensor chips are connected occurs. By analyzing the delay time of each sensor array, it is possible to specify the optical signal propagated through each sensor array.

The case where the first optical signal of the pulse is transmitted to the optical sensor system 1D, and the difference in the delay time of the received signal of the optical receiver unit 32 is analyzed, thereby identifying each sensor array has been described.

On the other hand, the first optical signal of continuous light in which a plurality of wavelengths are multiplexed may be transmitted to the optical sensor system 1D and the difference in wavelength included in the received signal of the optical receiver unit 32 may be analyzed, thereby identifying the optical sensor chip $\mathbf{21}_k$. In this case, the optical sensor system 1D does not need to include the optical path length adder unit 9.

As described above, the optical sensor system 1D according to the second embodiment includes the optical path length adder unit 9 that is an optical path provided between the optical sensor chip $\mathbf{21}_k$ and the optical sensor chip $\mathbf{21}_{k+1}$ in the optical sensor unit 2 and applies a delay for identifying the sensor array in which the plurality of optical sensor chips $\mathbf{21}_k$ are connected to the first optical signal.

By analyzing the delay time of the first optical signal, the optical sensor system 1D can identify the sensor array, and measure the state of the specimen 100 at the place where the sensor array is disposed. As a result, it is possible to extend the measurement range for measuring the state of the specimen 100.

In the optical sensor system 1D according to the second embodiment, the identification unit 41 identifies the plurality of optical sensor chips $\mathbf{21}_k$ by analyzing the wavelength of the optical signal propagating between the optical sensor chips $\mathbf{21}_k$ using the received signal of the optical receiver unit 32. As a result, the optical sensor system 1D can identify the individual optical sensor chips $\mathbf{21}_k$.

Third Embodiment

Figure 21:
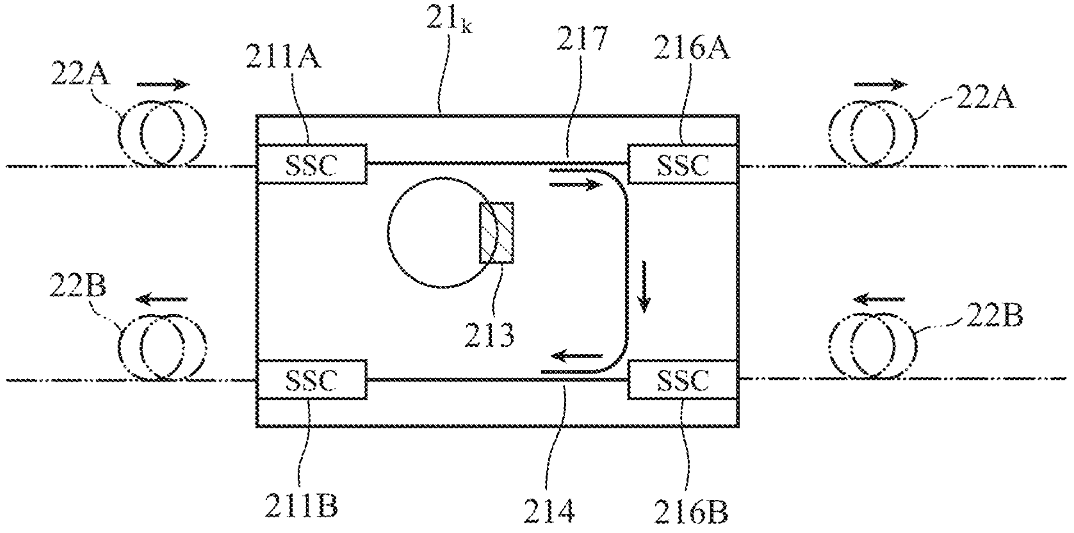
FIG. 21 is a configuration diagram illustrating an optical sensor chip and an optical waveguide according to a third embodiment.

FIG. 21 is a configuration diagram illustrating an optical sensor chip $\mathbf{21}_k$ according to a third embodiment. In FIG. 21, the optical sensor chip $\mathbf{21}_k$ according to the third embodiment includes the spot-size conversion unit 211A, the spot-size conversion unit 211B, the changer unit 213, the multiplexer unit 214, the spot-size conversion unit 216A, the spot-size conversion unit 216B, and an optical path folding unit 217.

The changer unit 213 changes the characteristics of the input first optical signal depending on the state of the specimen 100, and outputs the first optical signal with the changed characteristics. The characteristics of the first optical signal include an intensity characteristic, a phase characteristic, or a frequency characteristic. The changer unit 213 changes at least one of the intensity characteristic, the phase characteristic, or the frequency characteristic of the first optical signal.

For example, the changer unit 213 is implemented by a ring resonator that is an optical waveguide. Note that the changer unit 213 is only required to change the characteristics of the first optical signal depending on the state of the specimen 100, and may be a phase shifter including an optical waveguide, a frequency shifter including an optical waveguide, or an optical element including a combination of the phase shifter and the frequency shifter. Furthermore, the changer unit 213 may be a ring resonator, a Mach-Zehnder interferometer (MZI), or a combination thereof.

The optical path folding unit 217 is an optical path with a predetermined optical path length, the optical path propagating a part of the first optical signal changed by the changer unit 213 depending on the state of the specimen 100 and outputting the part of the first optical signal to the multiplexer unit 214. For example, in a case where the first optical signal is a pulse of an optical signal with a single wavelength, the optical path folding unit 217 outputs a part of the first optical signal changed depending on the state of the specimen 100 to the multiplexer unit 214.

In addition, the optical path folding unit 217 outputs the remaining part of the first optical signal changed by the changer unit 213 depending on the state of the specimen 100 to the spot-size conversion unit 216A instead of the multiplexer unit 214. For example, in the optical sensor chip $\mathbf{21}_k$, the first signal that has passed through the optical path folding unit 217 and is output to the spot-size conversion unit 216A is output to the optical sensor chip $\mathbf{21}_{k+1}$.

The multiplexer unit 214 multiplexes the first optical signal changed depending on the state of the specimen 100 and the second optical signal input by the spot-size conversion unit 216B. For example, the multiplexer unit 214 included in the optical sensor chip $\mathbf{21}_k$ multiplexes the first optical signal changed by the changer unit 213 depending on the state of the specimen 100 and the second optical signal input from the optical sensor chip $\mathbf{21}_{k+1}$. The optical signal in which the first optical signal and the second optical signal are multiplexed is output from the multiplexer unit 214 to the spot-size conversion unit 211B. For example, in the optical sensor chip $\mathbf{21}_k$, the optical signal in which the first optical signal is multiplexed is output to the optical sensor chip $\mathbf{21}_{k-1}$.

The first optical signal changed depending on the state of the specimen 100 propagates through the optical path with a predetermined optical path length when folded by the optical path folding unit 217, so that the first optical signal delayed from the first optical signal before transmission is multiplexed therewith. Therefore, the identification unit 41 calculates the propagation time of the received signal of the first optical signal by comparing the propagation of the pulse of the first optical signal before transmission with the propagation of the pulse of the received signal of the optical signal received by the optical receiver unit 32. Next, the identification unit 41 can identify the optical sensor chip $\mathbf{21}_k$ corresponding to the received signal of the second optical signal by specifying the identification number k corresponding to the calculated propagation time. The identification unit 41 can also specify the position of the optical sensor chip $21_k$ corresponding to the identification number k.

In addition, the identification unit 41 may associate the first optical signal changed depending on the state of the specimen 100 with the identification number k of the optical sensor chip $21_k$ by analyzing the wavelength of the first optical signal included in the received signal of the optical receiver unit 32.

For example, in a case where the first optical signal is an optical signal that is continuous light with a plurality of wavelengths, the optical path folding unit 217 outputs the first optical signal with a predetermined wavelength from the first optical signal changed depending on the state of the specimen 100 to the multiplexer unit 214. In a case where the optical path folding unit 217 extracts and folds the first optical signal with a predetermined wavelength, the identification unit 41 identifies the optical sensor chip $21_k$ corresponding to the wavelength by specifying the identification number k corresponding to the wavelength of the received signal of the optical receiver unit 32.

As described above, the optical sensor chip $21_k$ according to the third embodiment includes the optical path folding unit 217 that is an optical path with a predetermined optical path length, the optical path propagating a part of the first optical signal changed by the changer unit 213 depending on the state of the specimen 100 and outputting a part of the first optical signal to the multiplexer unit 214. The multiplexer unit 214 multiplexes a part of the first optical signal propagated through the optical path that is the optical path folding unit 217 and the second optical signal input by the spot-size conversion unit 216B. The spot-size conversion unit 216A outputs the remaining part of the first optical signal changed by the changer unit 213 depending on the state of the specimen 100 to the optical sensor chip $21_{k-1}$. The state of the specimen 100 measured by the optical sensor chip $21_k$ is specified by analyzing a change in the first optical signal depending on the state of the specimen 100. As a result, the optical sensor chip $21_k$ can be used to collectively measure the state of a plurality of portions of the specimen 100.

In addition, in the optical sensor chip $21_k$ according to the first to third embodiments, the changer unit 213 detects the state of the specimen 100 by optical processing, and components other than the changer unit 213 do not need electrical processing. Therefore, in the optical sensor systems 1 and 1A to 1D, it is not necessary to supply power to the individual optical sensor chips $21_k$, and it is possible to achieve a measurement system with low power consumption. Furthermore, since the state of the specimen 100 can be measured even when the optical sensor chips $21_k$ are arranged in a place where there is no power supply, it is possible to achieve an optical sensor system with a high degree of freedom in chip arrangement.

In addition, the ring resonator constituting the changer unit 213 illustrated in FIG. 8 may be replaced with an optical element having a phase shifter function or a frequency shifter function, or one ring resonator may have the phase shifter function or the frequency shifter function. For example, by stacking a member formed of a material different from the material of the waveguide 2132 on the waveguide 2132 that is a ring resonator, the changer unit 213 can change the characteristics of the optical signal depending on the material of the member stacked on the waveguide 2132.

For example, in a case where a magnetic body is stacked on the waveguide 2132, the phase of the optical signal circulated in the waveguide 2132 changes in proportion to the intensity of the magnetic field generated around the waveguide 2132. The waveguide effective refractive index $n_{eff}$ of the waveguide 2132 also changes depending on the change in the phase of the optical signal. The analysis unit 42 calculates the amount of shift A) of the resonance wavelength between the transmitted signal and the received signal using the relationship of $2\pi \times R \times \Delta n_{eff} = m \times \Delta\lambda$ in the waveguide 2132.

The analysis unit 42 calculates the amount of change $\Delta n_{eff}$ in the waveguide effective refractive index of the waveguide 2132 using the calculated amount of shift $\Delta\lambda$ in resonance wavelength, and calculates the intensity of the magnetic field using the calculated $\Delta n_{eff}$. As a result, the optical sensor chip $21_k$ can be used to detect the magnetic field from the specimen 100.

Furthermore, the waveguide 2132 may be a waveguide on which a member that changes the waveguide effective refractive index $n_{eff}$ by binding to DNA such as graphene is stacked. As a result, when DNA is present around the waveguide 2132, the phase of the optical signal circulated in the waveguide 2132 changes. The waveguide effective refractive index $n_{eff}$ of the waveguide 2132 also changes depending on the change in the phase of the optical signal. Similarly to the case of detecting the magnetic field, the analysis unit 42 calculates the amount of shift $\Delta\lambda$ in resonance wavelength between the transmitted signal and the received signal using the relationship of $2\pi \times R \times \Delta n_{eff} = m \times \Delta\lambda$ in the waveguide 2132. The analysis unit 42 calculates the amount of change $\Delta n_{eff}$ in the waveguide effective refractive index of the waveguide 2132 using the amount of shift $\Delta\lambda$ in resonance wavelength, and calculates the binding amount of DNA using the calculated $\Delta n_{eff}$. As a result, the optical sensor chip $21_k$ can be used to detect the DNA of the specimen 100.

In the optical sensor systems according to the first to third embodiments, by meandering the Z optical sensor chips $21_k$ continuously connected via the optical fiber 22, the optical sensor chips $21_k$ can be arranged in various shapes in the optical sensor unit 2, high degree of freedom in arrangement of the optical sensor chips $21_k$ is obtained, and the arrangement density is improved. As a result, the optical sensor unit 2 included in the optical sensor systems according to the first to third embodiments can be disposed even in a narrow space where the optical sensor unit is conventionally difficult to be disposed.

In the optical sensor systems according to the first to third embodiments, the modulated signal generator unit 33 may generate a modulated signal to be used to measure a state designated by a control signal among a plurality of types of states of the specimen 100, and output the generated modulated signal to the optical transmitter unit 31. The optical transmitter unit 31 generates a first optical signal to which modulation corresponding to the measurement of the state designated by the control signal has been applied. As a result, it is possible to measure the state of the specimen 100 using the first optical signal to which modulation corresponding to the measurement of the designated state has been applied. For example, the modulated signal generator unit 33 generates a phase modulated signal in a case where the moisture content of the specimen 100 is designated by the control signal, and generates a frequency modulated signal in a case where the temperature of the specimen 100 is designated by the control signal. As a result, it is possible to generate a first optical signal that has been phase-modulated to measure the moisture content of the specimen 100 or frequency-modulated to measure the temperature of the specimen 100.

The optical sensor systems according to the first to third embodiments may include a wireless signal transceiver unit that transmits and receives a wireless signal to and from an external device, and a modulation control unit that controls the generation of a modulated signal by the modulated signal generator unit 33. The modulation control unit demodulates the control signal received from the external device by the wireless signal transceiver unit, and outputs the demodulated control signal to the modulated signal generator unit 33. For example, the modulation control unit compensates for the degradation of the signal quality of the control signal from the external device, and outputs the control signal in which the degradation of the signal quality has been compensated to the modulated signal generator unit 33. More specifically, the modulation-demodulation control unit compensates for the degradation of the signal quality by performing error detection of a signal being wirelessly transmitted and corrects the detected error. The wireless signal transceiver unit is, for example, a communication device that performs short-range wireless communication such as Bluetooth (registered trademark) or a WiFi router.

Note that it is possible to combine the embodiments, modify any component of each embodiment, or omit any component of each embodiment.

INDUSTRIAL APPLICABILITY

The optical sensor chip according to the present disclosure can be used to measure the state of various specimens. For example, by interspersing a plurality of optical sensor chips according to the present disclosure on a corridor or a road, it is possible to collectively measure the state around the corridor or the road.

REFERENCE SIGNS LIST

1 and 1A to 1D: Optical sensor system, 2: Optical sensor unit, 3: Optical transceiver unit, 4: Received signal analyzer unit, 5: Display unit, 6A and 6B: Optical termination, 7A and 7B: Connector, 8A and 8B: Optical coupler, 9 and 215A: Optical path length adder unit, $\mathbf{21}_1$ to $\mathbf{21}_k$, $\mathbf{21}_{k-1}$, $\mathbf{21}_{Z-1}$, $\mathbf{21}_W$, $\mathbf{21}_X$, $\mathbf{21}_Y$, and $\mathbf{21}_Z$: Optical sensor chip, 22, 22A, and 22B: Optical fiber, 31: Optical transmitter unit, 32: Optical receiver unit, 33: Modulated signal generator unit, 41: Identification unit, 42: Analysis unit, 100 and 100C: Specimen, 100A: Person, 100B: Soil, 200: Bed, 211A, 211B, 216A, and 216B: Spot-size conversion unit, 212A: Optical path splitter unit, 213, 213A, and 213B: Changer unit, 214: Multiplexer unit, 217: Optical path folding unit, 400: Box, 1000: Input interface, 1001: Output interface, 1002: Processing circuit, 1003: Processor, 1004: Memory, 2131 to 2133: Waveguide

The invention claimed is:

1. An optical sensor chip capable of taking an arbitral connection form via a connector, comprising:

a first interface to receive a first optical signal from an outside via a transmission side optical fiber;

a changer to change the first optical signal depending on a state of a specimen;

a second interface to output the first optical signal to an adjacent optical sensor chip via the transmission side optical fiber;

a third interface to receive a second optical signal from the adjacent optical sensor chip via a reception side optical fiber;

a multiplexer to multiplex a first optical signal changed by the changer depending on the state of the specimen and the second optical signal received by the third interface; and a fourth interface to output an optical signal multiplexed by the multiplexer to the outside via the reception side optical fiber, wherein the connector connects the optical sensor chip to an adjacent optical sensor chip such that the second interface is connected to a first interface of the adjacent optical sensor chip, and the third interface is connected to a fourth interface of the adjacent optical sensor chip.

2. The optical sensor chip according to claim 1, wherein the first interface and the fourth interface constitute one interface for one side device, and the second interface and the third interface constitute one interface for another side device.

3. The optical sensor chip according to claim 1, further comprising:

a first optical path length adder as an optical path to delay a first optical signal output by the second interface; and a splitter to split a first optical signal received by the first interface or a first optical signal changed by the changer depending on a state of a specimen.

4. The optical sensor chip according to claim 1, wherein a first optical signal received by the first interface is an optical signal with one predetermined wavelength, and an electrical signal obtained by modulating one of an intensity characteristic, a phase characteristic, and a frequency characteristic is applied to the first optical signal.

5. The optical sensor chip according to claim 1, wherein a first optical signal received by the first interface is an optical signal with a plurality of wavelengths, and the optical sensor chip further comprises a splitter to select a first optical signal with a predetermined wavelength from the first optical signal received by the first interface and to output the first optical signal selected to the changer.

6. An optical sensor system comprising:

an optical sensor having a plurality of the optical sensor chips according to claim 1, in which the first interface and the second interface are connected via the transmission side optical fiber, and the third interface and the fourth interface are connected via the reception side optical fiber between adjacent optical sensor chips, and a specimen is disposed; and processing circuitry to:

transmit a first optical signal to the first interface of an optical sensor chip at an end portion of the optical sensor;

receive, from the fourth interface of the optical sensor chip at the end portion of the optical sensor, an optical signal in which a first optical signal changed depending on a state of the specimen is multiplexed;

identify individual optical sensor chips using a received signal; and specify the state of the specimen for each of the optical sensor chips by analyzing the received signal.

7. The optical sensor system according to claim 6, wherein the processing circuitry specifies a change in a first optical signal depending on a state of a specimen by analyzing any one of an intensity characteristic, a phase characteristic, a frequency characteristic, and a wavelength characteristic of a received signal.

8. The optical sensor system according to claim 6, wherein a plurality of optical sensor chips are continuously connected in the optical sensor, and the processing circuitry associates a first optical signal changed depending on a state of a specimen with an optical sensor chip by analyzing a delay time of a first optical signal included in a received signal.

9. The optical sensor system according to claim 6, wherein the processing circuitry associates a first optical signal changed depending on a state of a specimen with an optical sensor chip by analyzing a wavelength of a first optical signal included in a received signal.

10. The optical sensor system according to claim 6, further comprising a second optical path length adder as an optical path provided between optical sensor chips in the optical sensor to apply a delay for identifying a sensor array in which a plurality of optical sensor chips are connected to an optical signal propagating between the optical sensor chips.

11. The optical sensor system according to claim 10, wherein the processing circuitry identifies a sensor array in which a plurality of optical sensor chips are connected by analyzing a delay time of an optical signal propagating between the optical sensor chips using a received signal.

12. The optical sensor system according claim 6, wherein the processing circuitry identifies a plurality of optical sensor chips by analyzing a wavelength of an optical signal propagating between the optical sensor chips using a received signal.

13. A measurement method for an optical sensor system including:

an optical sensor having a plurality of the optical sensor chips according to claim 1, in which the first interface and the second interface are connected via the transmission side optical fiber, and the third interface and the fourth interface are connected via the reception side optical fiber between adjacent optical sensor chips; and processing circuitry, the measurement method comprising:

transmitting a first optical signal to the first interface of an optical sensor chip at an end portion of the optical sensor by the processing circuitry;

receiving, by the processing circuitry, an optical signal in which a first optical signal changed depending on a state of a specimen is multiplexed, from the fourth interface of the optical sensor chip at the end portion of the optical sensor;

identifying individual optical sensor chips using a received signal; and specifying the state of the specimen for each of the optical sensor chips by analyzing the received signal.

14. The optical sensor chip according to claim 1, wherein the transmission side optical fiber extends via the first interface and the second interface, and the reception side optical fiber extends via the third interface and the fourth interface.

* * * * *